(12) United States Patent
Tidwell et al.

(10) Patent No.: US 7,517,893 B2
(45) Date of Patent: Apr. 14, 2009

(54) BICHALCOPHENES AND THEIR PRODRUGS AS ANTIPROTOZOAL AGENTS

(75) Inventors: Richard R. Tidwell, Pittsboro, NC (US); David W. Boykin, Atlanta, GA (US); Chad Stephens, Augusta, GA (US); Mohamed A. Ismail, Atlanta, GA (US); W. David Wilson, Atlanta, GA (US); Reto Brun, Basel (CH); Karl Werbovetz, Colombus, OH (US)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 118 days.

(21) Appl. No.: 11/435,323

(22) Filed: May 16, 2006

(65) Prior Publication Data

US 2006/0293540 A1    Dec. 28, 2006

Related U.S. Application Data

(60) Provisional application No. 60/683,177, filed on May 20, 2005.

(51) Int. Cl.
*C07D 401/02* (2006.01)
*A61K 31/44* (2006.01)

(52) U.S. Cl. .................. 514/336; 514/387; 514/461; 546/268.1; 546/280.4; 546/283.4; 548/304.7; 549/472

(58) Field of Classification Search .............. None
See application file for complete search history.

(56) References Cited

FOREIGN PATENT DOCUMENTS

| WO | WO 96/40138 | 12/1996 |
|---|---|---|
| WO | WO 02/36588 A | 5/2002 |
| WO | WO 02/057224 A | 7/2002 |
| WO | WO 2004/050018 A | 6/2004 |
| WO | WO 2005/025565 A1 | 3/2005 |
| WO | WO 2005/033065 A | 4/2005 |

OTHER PUBLICATIONS

Partial European Search Report corresponding to an EP Application No. 06114189 dated Sep. 26, 2006.
Decision to grant a European patent pursuant to Article 97(1) EPC corresponding to Patent Application No. 06114189.1 - 2101 / 1726589 dated Sep. 18, 2008.

*Primary Examiner*—Zinna N Davis
(74) *Attorney, Agent, or Firm*—Jenkins, Wilson, Taylor & Hunt, P.A.

(57) ABSTRACT

Novel dicationic bichalcophene compounds are described. The presently disclosed novel dicationic bichalcophene compounds exhibit in vitro activity versus *Trypanosoma brucei rhodesiense, Plasmodium falciparum*, or *Leishmania donovani* comparable to that of pentamidine and furamidine. Some of the novel dicationic bichalcophene compounds displayed good activity in vivo in a murine model of a *Trypanosoma brucei rhodesiense* infection.

33 Claims, No Drawings

BICHALCOPHENES AND THEIR PRODRUGS AS ANTIPROTOZOAL AGENTS

CROSS REFERENCE TO RELATED APPLICATIONS

This application claims the benefit of and priority to U.S. Provisional Patent Application Ser. No. 60/683,177, filed May 20, 2005, the disclosure of which is incorporated herein by reference in its entirety.

TECHNICAL FIELD

The presently disclosed subject matter relates to methods for combating microbial infections with novel dicationic bichalcophene compounds and their prodrugs, processes for synthesizing novel dicationic bichalcophene compounds and their prodrugs, and the novel dicationic bichalcophene compounds and their prodrugs themselves.

ABBREVIATIONS

δ=chemical shift
Ac=acetyl
AcO=acetoxyl
AcOH=acetic acid
$Ac_2O$=acetic anhydride
Am=amidine
AmOH=amidoxime
Bu=butyl
° C.=degrees Celsius
calcd=calculated
cm=centimeters
$Cs_2CO_3$=cesium carbonate
dec=decomposition point
DIBAL=diisobutylaluminium hydride
DMF=dimethylformamide
DMSO=dimethylsulfoxide
$D_2O$=deuterium oxide
EIMS=electrospray-ionization mass spectrometry
EtOAc=ethyl acetate
EtOH=ethanol
g=grams
h=hours
HAT=human African trypanosomiasis
HCl=hydrogen chloride
HPLC=high-pressure liquid chromatography
Hz=hertz
ip=intraperitoneal
kg=kilograms
KO-t-Bu=potassium tert-butoxide
L. d.=*Leishmania donovani*
M=molar
Me=methyl
MeO=methoxyl
MHz=megahertz
min.=minutes
mL=milliliters
mm=millimeters
mM=millimolar
m.p.=melting point
MS=mass spectroscopy
$Na_2CO_3$=sodium carbonate
$Na_2SO_4$=sodium sulfate
NBS=N-bromosuccinimide
$NH_2OH.HCl$=hydroxylamine hydrochloride
NMR=nuclear magnetic resonance
p=para
PCP=*Pneumocystis carinii* pneumonia
Pd-C=10% palladium on carbon
$Pd(PPh_3)_4$=tetrakis(triphenylphosphine)palladium
P. f.=*Plasmodium falciparum*
po=oral
psi=pounds per square inch
spp.=species
T. b. r.=*Trypanosoma brucei rhodesiense*
T. cruzi=*Trypanosoma cruzi*
THF=tetrahydrofuran
TLC=thin-layer chromatography
TMS=trimethylsilyl
UV=ultraviolet

BACKGROUND

The antimicrobial activity of aromatic diamidines was first reported in the 1930's. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460. Since that time dicationic molecules have received considerable attention as potential new therapeutic agents. Despite these efforts, pentamidine, first reported in 1942, see Ashley, J. N., et al., *J. Chem. Soc.*, 103-106 (1942), is the only compound from this class of molecules for which there has been significant human use. Pentamidine is currently used against primary stage human African trypanosomiasis (HAT), antimony-resistant leishmaniasis and also as a secondary drug for AIDS-related *Pneumocystis carinii* pneumonia (PCP). See Tidwell, R. R. and Boykin. D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460. Pentamidine, however, must be administered parenterally, and causes potentially severe side effects. Further, drug resistance among parasites is emerging. Thus there continues to be a need for improvement in the art for additional compounds having desirable antimicrobial activity, whether against the representative pathogens referenced above or against other pathogens.

SUMMARY

In some embodiments, the presently disclosed subject matter provides compounds of Formula (I):

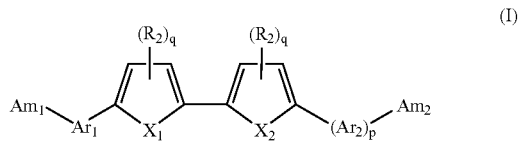

wherein:
X$_1$ and X$_2$ are independently selected from the group consisting of O, S, Se, Te, and NR$_1$, wherein R$_1$ is selected from the group consisting of H, alkyl, substituted alkyl, cycloalkyl, aryl, and substituted aryl;
p is an integer from 0 to 1;
each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;

$Ar_1$ and $Ar_2$ are independently selected from the group consisting of phenyl, pyridine, and benzimidazole;

$Am_1$ and $Am_2$ are each

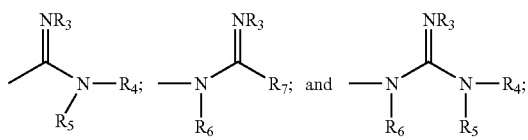

wherein:
each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_4$ together represent a $C_2$ to $C_{10}$ alkyl, $C_2$ to $C_{10}$ hydroxyalkyl, or $C_2$ to $C_{10}$ alkylene; or $R_3$ and $R_4$ together are:

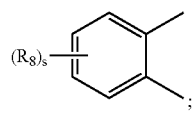

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments, $Ar_1$ and $Ar_2$ are each independently selected from the group consisting of phenyl and pyridine, and the compound of Formula (I) has the following structure:

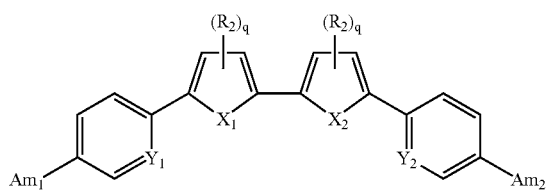

wherein:
$Y_1$ and $Y_2$ are each independently selected from the group consisting of CH and N;
or a pharmaceutically acceptable salt thereof.

In some embodiments, $Ar_1$ is selected from the group consisting of phenyl and pyridine and $Ar_2$ is benzimidazole, and the compound of Formula (I) has the following structure:

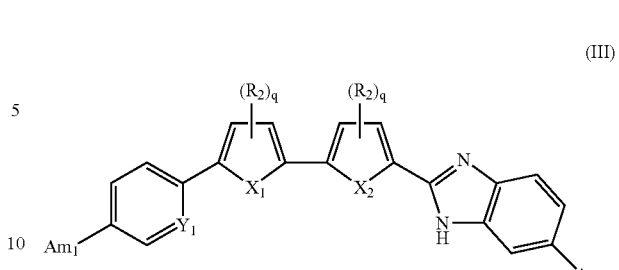

wherein:
$Y_1$ is selected from the group consisting of CH and N;
or a pharmaceutically acceptable salt thereof.

In some embodiments, p is 0 and the compound of Formula (I) has the following structure:

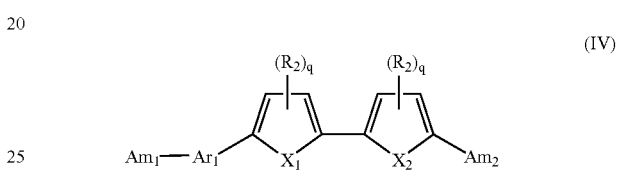

or a pharmaceutically acceptable salt thereof.

In some embodiments, the presently disclosed subject matter provides the use of an active compound as described hereinabove, e.g., a compound of Formula (I-IV), for the preparation of a medicament for treating a microbial infection.

In some embodiments, the presently disclosed subject matter provides a pharmaceutical formulation comprising a compound of Formula (I-IV).

In some embodiments, the presently disclosed subject matter provides a method of preparing compounds of Formula (I-IV).

It is accordingly an object of the presently disclosed subject matter to provide methods and compositions for treating microbial infections, such as, but not limited to, those caused by *Trypanosoma* species (spp.), including, but not limited to, *Trypanosoma brucei rhodesiense*, *Trypanosoma brucei gambiense*, *Trypanosoma brucei brucei*, and *Trypanosoma cruzi*; *Plasmodium* spp., including, but not limited to *Plasmodium falciparum*; and *Leishmania* spp., including, but not limited to *Leishmania donovani* and *Leishmania mexicana amazonensis*, in a subject in need thereof. It is another object of the presently disclosed subject matter to provide a process for synthesizing compounds for treating microbial infections such as, but not limited to, those caused by *Trypanosoma* species, *Plasmodium* species and *Leishmania* species.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

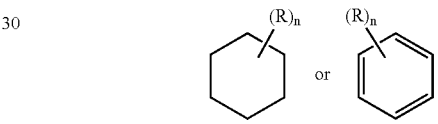

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

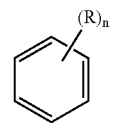

wherein n is an integer from 0 to 2 comprises compound groups including, but not limited to:

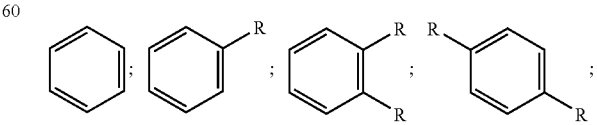

and the like.

The structure:

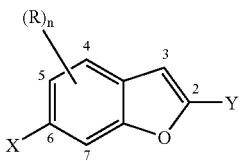

wherein n is one (1) comprises compound groups including:

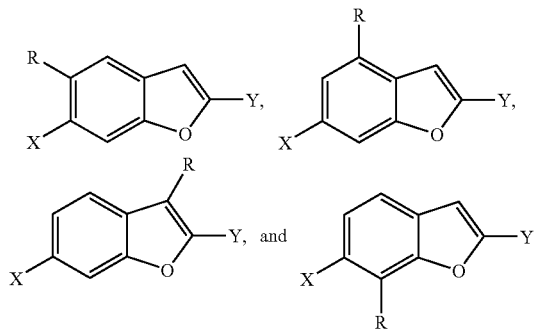

wherein the one (1) R substituent can be attached at any carbon on the benzofuran parent structure not occupied by another designated substituent, as in this case carbon 6 is substituted by X and carbon 2 is substituted by Y.

A dashed line representing a bond in a cyclic ring structure indicates that the bond can be either present or absent in the ring. That is a dashed line representing a bond in a cyclic ring structure indicates that the ring structure is selected from the group consisting of a saturated ring structure, a partially saturated ring structure, and an unsaturated ring structure.

In some embodiments, the compounds described by the presently disclosed subject matter contain a linking group. As used herein, the term "linking group" comprises a chemical moiety, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —NH$_2$ group. The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "R'," "X," "Y," "Y'", "A," "A'", "B," "L," or "Z" group will generally have the structure that is recognized in the art as corresponding to a group having that name, unless specified otherwise herein. For the purposes of illustration, certain representative "R," "X," and "Y" groups as set forth above are defined below. These definitions are intended to supplement and illustrate, not preclude, the definitions that would be apparent to one of ordinary skill in the art upon review of the present disclosure.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "metal alkyl" refers to a compound of the general formula MR$_n$, wherein M is a metal atom, including, but not limited to aluminum, boron, magnesium, zinc, gallium, indium, and related metals, R is an alkyl group as defined herein, and n is an integer. A representative metal alkyl is trimethylaluminum, abbreviated as Al(CH$_3$)$_3$ or AlMe$_3$.

The term "alkali metal alcoholate" refers to an alkali metal derivative of an alcohol having the general formula M$_a$OR$_n$, wherein M$_a$ is an alkali metal, such as lithium, sodium, or potassium, O is oxygen, R is an alkyl group as defined herein, and n is an integer. Representative alkali metal alcoholates include, but are not limited to, sodium methanolate, abbreviated as NaOCH$_3$ or NaOMe, and potassium butoxide, abbreviated as KOC(CH$_3$)$_3$.

The term "acid anhydride" refers to an anhydride of an organic acid and includes, but is not limited to acetic anhydride ((CH$_3$C=O)$_2$O or Ac$_2$O) and benzoic anhydride ((C$_6$H$_5$C=O)$_2$O).

II. Novel Compounds

The structures of pentamidine, furamidine, and a representative structure of the presently disclosed bichalcophenes are shown in Scheme 1.

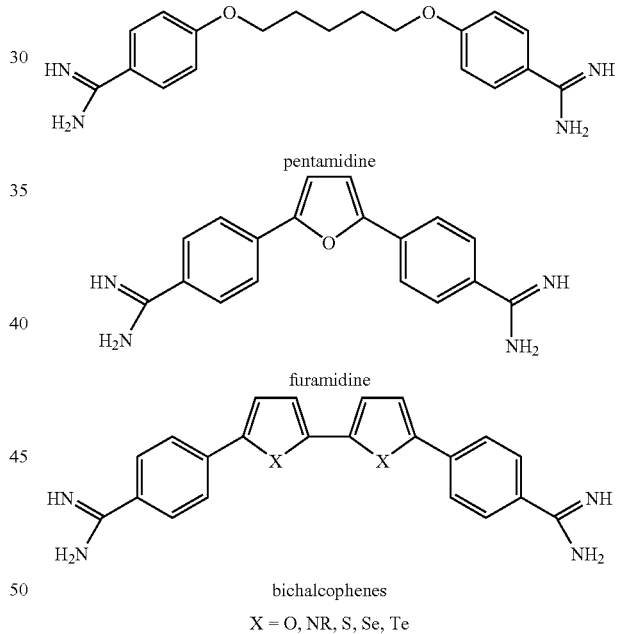

Scheme 1. Structures of Representative Dicationic Antiprotozoan Agents.

pentamidine furamidine bichalcophenes

X = O, NR, S, Se, Te

An orally effective prodrug of furamidine is currently in Phase II clinical trials against malaria, HAT and PCP. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460; Fairlamb, A. H., *Trends Parasitol.*, 19, 488-494 (2003); Bouteille, B., et al., *Fundam. Clin. Pharmacol.*, 17, 171-181 (2003). This type of dicationic molecule is thought to act by binding in the minor groove of DNA at AT rich sites, leading to inhibition of DNA dependant enzymes or possibly direct inhibition of transcription. See Tidwell, R. R. and Boykin, D. W., Dicationic DNA Minor Groove Binders as Antimicrobial Agents, in *Small*

Molecule DNA and RNA Binders: From Synthesis to Nucleic Acid Complexes, vol. 2, (M. Demeunynck, C. Bailly, and W. D. Wilson, ed., Wiley-VCH, New York, 2003), pp. 416-460; Dykstra, C. C. et al., Antimicrob. Agents Chemother., 38, 1890-1898 (1994); Bailly, C. et al., Anti-Cancer Drug Design, 14, 47-60 (1999); Fitzgerald, D. J. and Anderson, J. N., J. Biol. Chem., 274, 27128-27138 (1999); Henderson, D. and Hurley, L. H., Nature Med., 1, 525-527 (1995). While it is not desired to be bound to any particular theory, it is suggested that the selectivity of furamidine analogs, at least for trypanosomes, likely includes a cell entry component involving amidine transporters.

An element in the design of new potential aromatic diamidine therapeutics has been that the molecular scaffold bearing the amidine units should present crescent shape geometry complimentary to the curve of the minor groove of DNA. See Corey, M., et al., J. Med. Chem., 35, 431-438, (1992). Van der Waals contacts with the walls of the groove have been shown to contribute to binding affinity. See Czarny, A. D., et al., J. Am. Chem. Soc., 117, 4716 (1995); Mazur, S. F., et al., J. Mol. Bio., 300, 321-337 (2000); Wilson, W. D., et al., J. Am. Chem. Soc., 120, 10310-10321 (1998). A current theoretical analysis of the binding interactions of 25 minor groove binders shows that the small molecule curvature provides energetically favorable Van der Waals contacts. See Shaikh, S. A., et al., Arch. Biochem. Biophys., 429, 81-99 (2004). Pentamidine, furamidine and many analogs meet this crescent shape profile. See Tidwell, R. R. and Boykin, D. W., Dicationic DNA Minor Groove Binders as Antimicrobial Agents, in Small Molecule DNA and RNA Binders: From Synthesis to Nucleic Acid Complexes, vol. 2, (M. Demeunynck, C. Bailly, and W. D. Wilson, ed., Wiley-VCH, New York, 2003), pp. 416-460; Cory, M., et al., J. Med. Chem., 35, 431-438 (1992); Boykin, D. W., et al., J. Med. Chem., 41, 124-129 (1998); Boykin, D. W., et al., J. Med. Chem., 38, 912 (1995); Das, B. P. and Boykin, D. W., J. Med. Chem., 20, 531 (1977).

In some embodiments, the presently disclosed subject matter describes the expansion of the central core of furamidine to include an additional 5-membered heterocyclic ring to provide novel diamidines in the 2,5'-diarylbichalcophene series. In some embodiments, the presently disclosed compounds can maintain the approximate curvature that is desirable for groove binding, and can increase base pair coverage.

II.A. Compounds of Formula (I-IV)

Described herein are compounds of Formula (I):

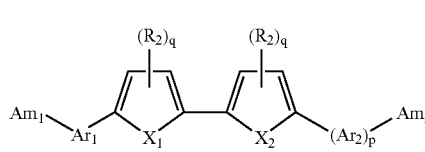

(I)

wherein:
$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
p is an integer from 0 to 1;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Ar_1$ and $Ar_2$ are independently selected from the group consisting of phenyl, pyridine, and benzimidazole;
$Am_1$ and $Am_2$ are each

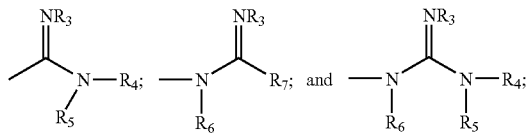

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

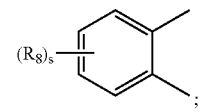

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments of compounds of Formula (I), $Ar_1$ and $Ar_2$ are selected from the group consisting of phenyl and pyridine and the compound of Formula (I) has the following structure:

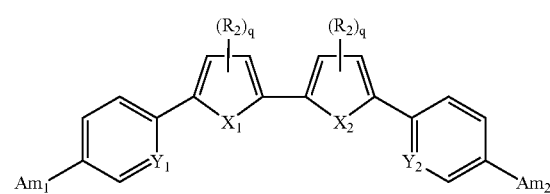

(II)

wherein:
$X_1$ and $X_2$ are independently selected from the group consisting of O, S, Se, Te, and $NR_1$, wherein $R_1$, is selected from the group consisting of H, alkyl, substituted alkyl, cycloalkyl, aryl, and substituted aryl;
$Y_1$, and $Y_2$ are each independently selected from the group consisting of CH and N;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Am_1$ and $Am_2$ are each

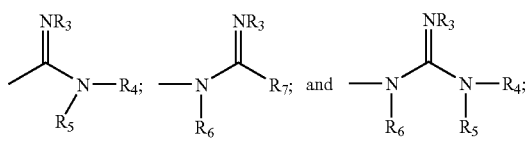

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

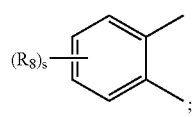

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;
or a pharmaceutically acceptable salt thereof.

In some embodiments of compounds of Formula (I), $Ar_1$ is selected from the group consisting of phenyl and pyridine and $Ar_2$ is benzimidazole; and the compound of Formula (I) has the following structure:

(III)

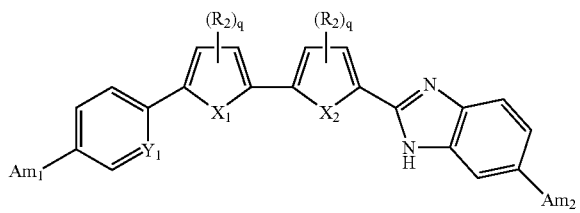

wherein:
$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
$Y_1$ is selected from the group consisting of CH and N;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Am_1$ and $Am_2$ are each

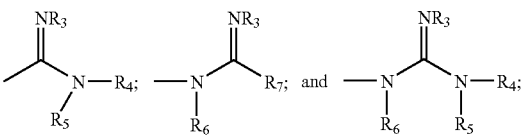

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

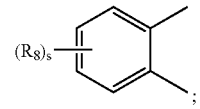

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;
or a pharmaceutically acceptable salt thereof.

In some embodiments of compounds of Formula (I), p is 0 and the compound of Formula (I) has the following structure:

(IV)

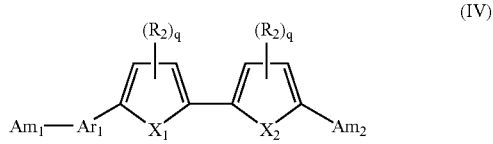

wherein:
$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
$Ar_1$ is selected from the group consisting of phenyl, pyridine, and benzimidazole;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Am_1$ and $Am_2$ are each

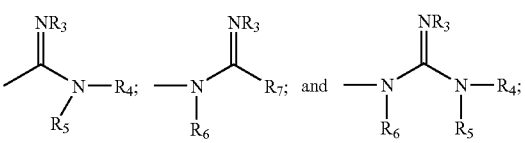

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

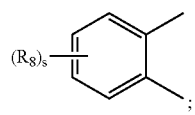

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;
or a pharmaceutically acceptable salt thereof.

In some embodiments, $X_1$ and $X_2$ are each oxygen. In some embodiments $X_1$ and $X_2$ are each sulfur. In some embodiments, $X_1$ and $X_2$ are each selenium.

In some embodiments, $R_4$ and $R_5$ are each H.

In some embodiments, $R_3$ is H. In some embodiments, $R_3$ is OH. In some embodiments, $R_3$ is $OCH_3$.

In some embodiments, the compound of Formula (I-IV) comprises a pharmaceutically acceptable salt. In some embodiments, the pharmaceutically acceptable salt comprises a hydrochloride salt. In some embodiments, the pharmaceutically acceptable salt comprises an acetate salt. In some embodiments, the pharmaceutically acceptable salt comprises a maleate salt.

II.B. Prodrugs

In representative embodiments, compounds disclosed herein are prodrugs. A prodrug means a compound that, upon administration to a recipient, is capable of providing (directly or indirectly) a compound of the presently disclosed subject matter or an inhibitorily active metabolite or residue thereof. Prodrugs can increase the bioavailability of the compounds of the presently disclosed subject matter when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. A number of the compounds (e.g., 6, 7, 13, 16, 19, 23, 32, and 39) disclosed herein are prodrugs.

II.C. Pharmaceutically Acceptable Salts

Additionally, the active compounds as described herein can be administered as pharmaceutically acceptable salts. Such pharmaceutically acceptable salts include the gluconate, lactate, acetate, tartarate, citrate, phosphate, maleate, borate, nitrate, sulfate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, as described in more detail herein below, the hydrochloride salt of an amidoxime compound is made by passing hydrogen chloride gas into an ethanolic solution of the free base. In some embodiments, as described in more detail herein below, the acetate salt of the presently disclosed diamidine compounds and/or the corresponding N-methoxy analogues are made directly from the appropriate N-hydroxy analogue. In some embodiments, as described herein below, the maleate salt of the N-methoxy analogue of a diamidine compound is prepared by heating the N-methoxy analogue with maleic acid in an alcohol for a period of time. Accordingly, in some embodiments, the pharmaceutically acceptable salt is a hydrochloride salt. In some embodiments, the pharmaceutically acceptable salt is an acetate salt. In some embodiments, the pharmaceutically acceptable salt is a maleate salt.

III. Pharmaceutical Formulations

The compounds of Formula (I-IV), the pharmaceutically acceptable salts thereof, prodrugs corresponding to compounds of Formula (I-IV), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations for administration, for example, as by intravenous or intramuscular injection.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the present methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formula (I-IV) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I-IV) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I-IV), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods for Treating Microbial Infections

Subjects with microbial infections can be treated by methods described herein. Such infections can be caused by a variety of microbes, including fungi, algae, protozoa, bacteria, and viruses. Exemplary microbial infections that can be treated by the method of the presently disclosed subject matter include, but are not limited to, infections caused by *Trypanosoma* spp. (e.g., *Trypanosoma brucei rhodesiense*, *Trypanosoma brucei gambiense*, *Trypanosoma brucei brucei*, and *Trypanosoma cruzi*), *Plasmodium* spp. (e.g., *Plasmodium falciparum*), *Mycobacterium tuberculosis*, *Pneumocystis carini*, *Giardia lamblia*, *Cryptosporidium parvum*, *Cryptococcus neoformans*, *Candida albicans*, *Candida tropicalis*, *Salmonella typhimurium*, *Leishmania donovani*, and *Leishmania mexicana amazonensis*. As used herein the terms *Trypanosoma* spp., *Plasmodium* spp., and *Leishmania* spp. encompass microbes classified under the genera *Trypanosoma*, *Plasmodium*, and *Leishmania* respectively. The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

The methods for treating microbial infections comprise administering to a subject in need thereof an active compound as described herein. These active compounds, as set forth above, include compounds of Formula (I-IV), their corresponding prodrugs, and pharmaceutically acceptable salts of the compounds and prodrugs.

With regard to the presently described method embodiments, compounds of Formula (I) are defined as having a structure as follows:

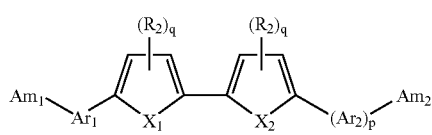
(I)

wherein:

$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;

p is an integer from 0 to 1;

each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;

$Ar_1$ and $Ar_2$ are independently selected from the group consisting of phenyl, pyridine, and benzimidazole;

$Am_1$ and $Am_2$ are each

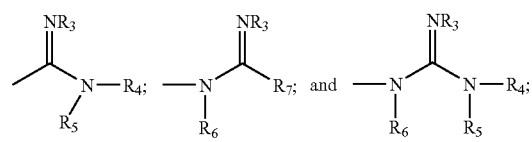

wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_4$ together represent a $C_2$ to $C_{10}$ alkyl, $C_2$ to $C_{10}$ hydroxyalkyl, or $C_2$ to $C_{10}$ alkylene; or $R_3$ and $R_4$ together are:

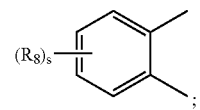

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments, $Ar_1$ and $Ar_2$ are selected from the group consisting of phenyl and pyridine and the compound of Formula (I) has the following structure:

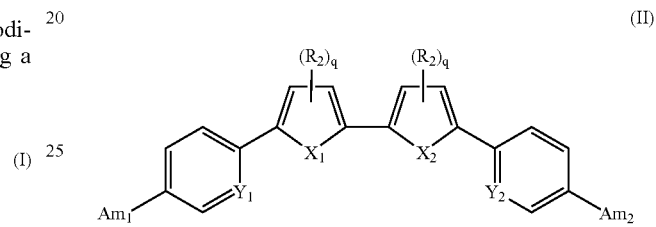
(II)

wherein:

$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;

$Y_1$ and $Y_2$ are each independently selected from the group consisting of CH and N;

each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;

$Am_1$ and $Am_2$ are each

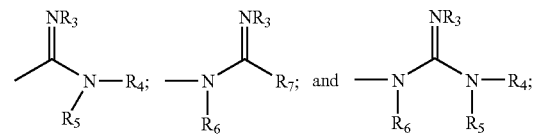

wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_4$ together represent a $C_2$ to $C_{10}$ alkyl, $C_2$ to $C_{10}$ hydroxyalkyl, or $C_2$ to $C_{10}$ alkylene; or $R_3$ and $R_4$ together are:

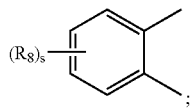

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments, $Ar_1$ is selected from the group consisting of phenyl and pyridine and $Ar_2$ is benzimidazole; and the compound of Formula (I) has the following structure:

(III)

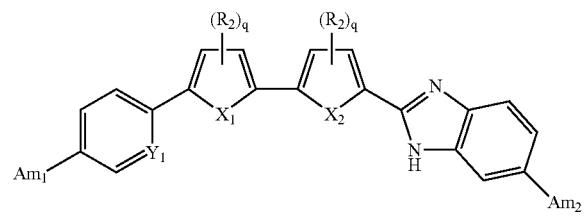

wherein:

$X_1$ and $X_2$ are independently selected from the group consisting of O, $NR_1$, S, Se, and Te; and wherein $R_1$ is selected from the group consisting of H, alkyl, substituted alkyl, cycloalkyl, aryl, and substituted aryl;

$Y_1$ is selected from the group consisting of CH and N;

each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;

$Am_1$ and $Am_2$ are each

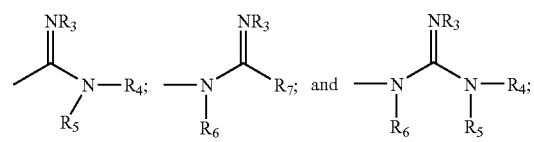

wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_4$ together represent a $C_2$ to $C_{10}$ alkyl, $C_2$ to $C_{10}$ hydroxyalkyl, or $C_2$ to $C_{10}$ alkylene; or $R_3$ and $R_4$ together are:

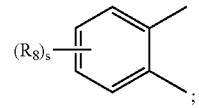

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments, p is 0 and the compound of Formula (I) has the following structure:

(IV)

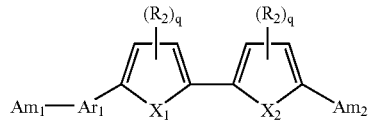

wherein:

$X_1$ and $X_2$ are independently selected from the group consisting of O, $NR_1$, S, Se, and Te; and wherein $R_1$ is selected from the group consisting of H, alkyl, substituted alkyl, cycloalkyl, aryl, and substituted aryl;

$Ar_1$ is selected from the group consisting of phenyl, pyridine, and benzimidazole;

each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;

$Am_1$ and $Am_2$ are each

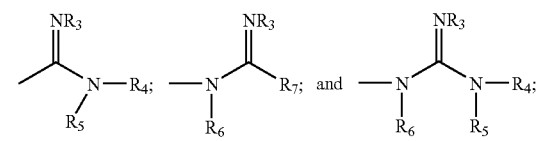

wherein:

each $R_3$ is independently selected from the group consisting of H, hydroxyl, acyloxyl, and alkoxyl;

each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_3$ and $R_4$ together represent a $C_2$ to $C_{10}$ alkyl, $C_2$ to $C_{10}$ hydroxyalkyl, or $C_2$ to $C_{10}$ alkylene; or $R_3$ and $R_4$ together are:

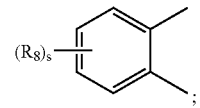

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

In some embodiments, the compound of Formula (I-IV) is administered in the form of a pharmaceutically acceptable salt. In some embodiments, the pharmaceutically acceptable salt comprises a hydrochloride salt. In some embodiments, the pharmaceutically acceptable salt comprises an acetate salt. In some embodiments, the pharmaceutically acceptable salt comprises a maleate salt.

In some embodiments, the microbial infection comprises an infection caused by a *Trypanosoma* spp., including, but not limited to, *Trypanosoma brucei rhodesiense, Trypanosoma brucei gambiense, Trypanosoma brucei brucei*, and *Trypanosoma cruzi*. In some embodiments, the microbial infection comprises a *Plasmodium falciparum* infection. In some embodiments, the microbial infection comprises an infection caused by a *Leishmania* spp., including, but not limited to, *Leishmania donovani* and *Leishmania mexicana amazonensis*.

In some embodiments, the compound of Formula (I-IV) is administered to a subject with an existing microbial infection. In some embodiments, the compound of Formula (I-IV) is administered prophylactically to prevent a microbial infection or to prevent the recurrence of a microbial infection. Thus, in some embodiments, the compound of Formula (I-IV) is administered prophylactically to prevent or reduce the incidence of one of: (a) a microbial infection in a subject at risk of infection; (b) a recurrence of the microbial infection; and (c) combinations thereof.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment and/or prevention of infectious diseases in warm-blooded vertebrates. Thus, the methods can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

V. General Processes for the Synthesis of Compounds of Formula (I-IV)

The synthetic procedures provided herein below comprise representative embodiments of novel methods of producing the presently disclosed compounds. The methods are outlined in Schemes 2-11 presented herein below and representative, non-limiting details are described in the Examples.

In some embodiments, the presently disclosed subject matter provides a method for preparing a compound of Formula (I) and pharmaceutically acceptable salts thereof, the method comprising:
(a) contacting a first cyano-substituted heterocyclic compound with N-bromosuccinimide to form a first bromo-heterocyclic compound;
(b) coupling the first bromo-heterocyclic compound with a second heterocyclic compound to form a third heterocyclic compound;
(c) reacting the third heterocyclic compound with one of:
  (i) a strong acid and an anhydrous alcohol, followed by ammonia and an anhydrous alcohol to form a compound of Formula (I), wherein the compound of Formula (I) is a bis-amidine;
  (ii) hydroxylamine hydrochloride and a base to form a compound of Formula (I), wherein the compound of Formula (I) is a bis-amidoxime; and
  (iii) a lithium bis(trialkylsilyl)amide for a period of time, followed by a strong acid for a period of time to form a compound of Formula (I), wherein the compound of Formula (I) is a bis-amidine.

In some embodiments, the method described immediately hereinabove further comprises:
(a) reacting the third heterocyclic compound with N-bromosuccinimide to form a second bromo-heterocyclic compound;
(b) contacting the second bromo-heterocyclic compound with one of:
  (i) cuprous cyanide to form a dinitrile; and
  (ii) a cyano-substituted arylboronic acid and a palladium catalyst to form a dinitrile;
(c) reacting the dinitrile with one of:
  (i) a strong acid and an anhydrous alcohol to form an intermediate di-imidate, followed by ammonia and an anhydrous alcohol to form a compound of Formula (I), wherein the compound of Formula (I) is a bis-amidine;
  (ii) hydroxylamine hydrochloride and a base to form a compound of Formula (I), wherein the compound of Formula (I) is a bis-amidoxime; and
  (iii) a lithium bis(trialkylsilyl)amide for a period of time, followed by a strong acid and an alcohol for a period of time to form a compound of Formula (I), wherein the compound of Formula (I) is a bis-amidine.

In some embodiments, the initially described method further comprises:
(a) reacting the third heterocyclic compound with phosphorus oxychloride to form a heterocyclic aldehyde;
(b) contacting the heterocyclic aldehyde with 3,4-diaminobenzonitrile and 1,4 benzoquinone to form a benzimidazole;
(c) reacting the benzimidazole with one of:
  (i) a strong acid and an alcohol to form an intermediate di-imidate, followed by ammonia and an alcohol to form a compound of Formula (I), wherein the compound of Formula (I) is a bis-amidine;
  (ii) hydroxylamine hydrochloride and a base to form a compound of Formula (I), wherein the compound of Formula (I) is a bis-amidoxime; and
  (iii) a lithium bis(trialkylsilyl)amide for a period of time, followed by a strong acid for a period of time to form a compound of Formula (I), wherein the compound of Formula (I) is a bis-amidine.

In some embodiments, the initially described method further comprises:

(a) contacting the first bromo-heterocyclic compound with hydroxylamine hydrochloride and a base to form an amidoxime;

(b) alkylating the amidoxime with a dialkyl sulfate to form a N-alkoxyamidine; and (c) coupling two N-alkoxyamidines to form a compound of Formula (I), wherein the compound of Formula (I) is a bis-N-alkoxyamidine.

In some embodiments, the initially described method further comprises:

(a) contacting the first bromo-heterocyclic compound with cuprous cyanide to form a dinitrile; and (b) contacting the dinitrile with hydroxylamine hydrochloride and a base to form a compound of Formula (I), wherein the compound of Formula (I) is a bis-amidoxime.

In some embodiments, bis-amidoxime compounds of Formula (I) prepared by the methods above can be further elaborated to form bis-amidines of Formula (I) by the method comprising:

(a) contacting the bis-amidoxime with acetic acid and acetic anhydride to form a compound of Formula (I), wherein the compound of Formula (I) is a bis-acetoxyamidine; and (b) contacting the bis-acetoxyamidine with a palladium-on-carbon catalyst, hydrogen gas, acetic acid, and an alcohol to form a compound of Formula (I), wherein the compound of Formula (I) is a diamidine.

In some embodiments, the first cyano-substituted heterocyclic compound is selected from the group consisting of 2-(4-cyanophenyl)furan, 6-(furan-2-yl)nicotinonitrile, 2-(4-cyanophenyl)thiophene, 6-(thiophen-2-yl)nicotinonitrile, 2-(4-cyanophenyl)selenophene, 6-(selenophen-2-yl)nicotinonitrile, and 2-(4-cyanophenyl)-5-(thiophen-2-yl)thiophene.

In some embodiments, the second heterocyclic compound is selected from the same group as the first cyano-substituted heterocyclic compound.

In some embodiments, the base comprises potassium tert-butoxide.

In some embodiments, the strong acid comprises hydrochloric acid.

In some embodiments, the lithium bis(trialkylsilyl)amide comprises lithium bis(trimethylsilyl)amide.

In some embodiments, the alcohol comprises an alkyl alcohol. In some embodiments, the alkyl alcohol is selected from the group consisting of ethanol and methanol.

In some embodiments, the dialkyl sulfate comprises dimethyl sulfate.

In some embodiments, the palladium catalyst comprises tetrakis(triphenylphosphine)palladium.

In some embodiments, the presently disclosed subject matter provides a method for preparing a compound of Formula (I) and pharmaceutically acceptable salts thereof, the method comprising:

(a) contacting a halo-substituted five-membered aromatic heterocyclic aldehyde with hydroxylamine hydrochloride and acetic anhydride to form a 2-cyano-5-halo-heteroaryl compound;

(b) coupling the 2-cyano-5-halo-heteroaryl compound with a trialkyltin-substituted five-membered aromatic heterocycle acetal to form a cyano-substituted diaryl aldehyde;

(c) contacting the cyano-substituted diaryl aldehyde with 3,4-diaminobenzonitrile and 1,4-benzoquinone to form a benzimidazole;

(d) contacting the benzimidazole with one of:

(i) a strong acid and an alcohol to form an intermediate di-imidate, followed by ammonia and an alcohol to form a compound of Formula (1), wherein the compound of Formula (I) is a bis-amidine;

(ii) hydroxylamine hydrochloride and a base to form a compound of Formula (1), wherein the compound of Formula (I) is a bis-amidoxime; and (iii) a lithium bis(trialkylsilyl)amide for a period of time, followed by a strong acid for a period of time to form a compound of Formula (1), wherein the compound of Formula (I) is a bis-amidine.

In some embodiments, the halo-substituted five-membered aromatic heterocyclic aldehyde is 5-bromo-2-furaldehyde.

In some embodiments, the base comprises potassium tert-butoxide.

In some embodiments, the strong acid comprises hydrochloric acid.

In some embodiments, the lithium bis(trialkylsilyl)amide comprises lithium bis(trimethylsilyl)amide.

In some embodiments, the alcohol comprises an alkyl alcohol. In some embodiments, the alkyl alcohol is selected from the group consisting of ethanol and methanol.

In some embodiments, the dialkyl sulfate comprises dimethyl sulfate.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Methods and Materials

Melting points were recorded using a Thomas-Hoover (Uni-Melt) capillary melting point apparatus and are uncorrected. TLC analysis was carried out on silica gel 60 $F_{254}$ precoated aluminum sheets and detected under UV light. $^1H$ and $^{13}C$ NMR spectra were recorded employing a Varian Unity Plus 300 spectrometer, and chemical shifts ($\delta$) are in ppm relative to TMS as internal standard. Mass spectra were recorded on a VG analytical 70-SE spectrometer. Elemental analyses were obtained from Atlantic Microlab Inc. (Norcross, Georgia, United States of America) or GSU CHN unit and are within ±0.4 of the theoretical values. All chemicals and solvents were purchased from Aldrich Chemical Co., Fisher Scientific. The syntheses of compounds 9 and 24b were previously described. See Ismail, M. A., et al., *J. Med. Chem.*, 46, 4761-4769 (2003). Compounds 1, 24a, 27a, and 27b can be prepared via analogous methods.

Example 1

5′-(4-Amidinophenyl)-2,2′-bifuran-5-carboxamidine

Scheme 2.
Synthesis of 5′-(4-Amidinophenyl)-2,2′-bifuran-5-carboxamidine.

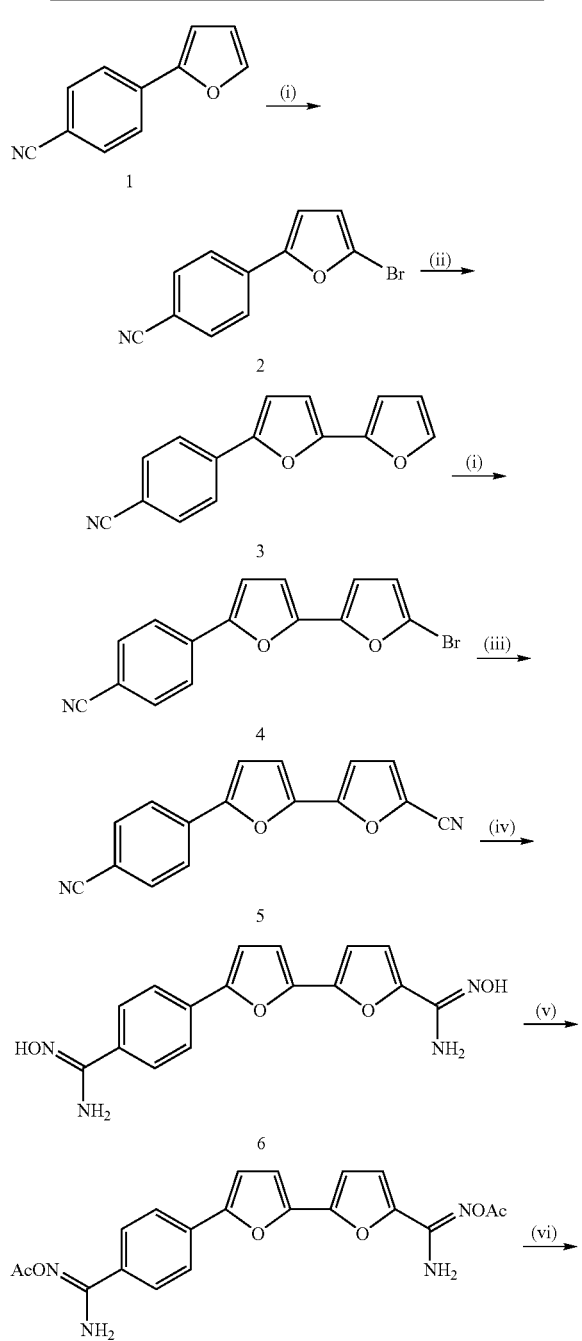

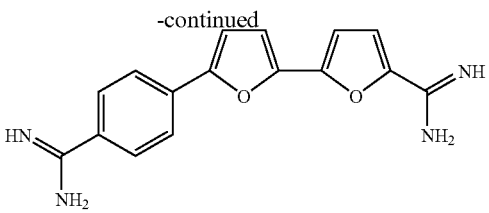

Reagents and conditions: (i) NBS, DMF; (ii) 2-tributyltin furan, Pd(PPh₃)₄; (iii) CuCN, DMF, 110-120° C.; (iv) NH₂OH•HCl, KO-t-Bu, DMSO; (v) AcOH/Ac₂O; (vi) H₂/Pd—C, AcOH.

4-(5-Bromofuran-2-yl)-benzonitrile (2). Referring now to Scheme 2 above, to a solution of 1 (8.45 g, 50 mmol) in DMF (30 mL) was added portionwise N-bromosuccinimide (9.79 g, 55 mmol) with stirring. The reaction mixture was stirred overnight, then poured onto cold water. The precipitate which formed was collected, washed with water and dried to give the analytically pure product 2 in 94.2% yield, mp 94-94.5° C. $^1$H NMR (CDCl$_3$); δ 6.45 (d, J=3.6 Hz, 1H), 6.76 (d, J=3.6 Hz, 1H), 7.66 (d, J=8.4 Hz, 2H), 7.70 (d, J=8.4 Hz, 2H). $^{13}$C NMR (CDCl$_3$); δ 153.7, 133.5, 132.6, 123.8, 123.6, 118.7, 114.0, 110.7, 110.3. EIMS (m/z, rel.int.); 247 (M$^+$, 50), 140 (100), 113 (10). Calcd for C$_{11}$H$_6$BrNO: C, 53.26; H, 2.44; N, 5.64. Found. C, 53.22; H, 2.43; N, 5.59.

4-(2,2′-Bifuran-5-yl)-benzonitrile (3). A mixture of 2 (2.48 g, 10 mmol), 2-tributyltin furan (3.58 g, 10 mmol), and tetrakis(triphenylphosphine)palladium (200 mg) in dry dioxane (60 mL) was heated under nitrogen at reflux (100-110° C.) for 24 h. The solvent was evaporated under reduced pressure and the resulting solid was dissolved in ethyl acetate. This solution was passed through celite to remove Pd. The solution was evaporated, and the solid was collected via filtration and washed with hexanes to furnish compound 3 in 79.5% yield, mp 104-105° C. $^1$H NMR (CDCl$_3$); δ 6.51 (dd, J=3.6 Hz, J=1.8 Hz, 1H), 6.68 (m, 2H), 6.87 (d, J=3.6 Hz, 1H), 7.46 (d, J=1.8 Hz, 1H), 7.66 (d, J=8.4 Hz, 2H), 7.77 (d, J=8.4 Hz, 2H). $^{13}$C NMR (CDCl$_3$); δ 150.9, 147.5, 145.8, 142.4, 134.1, 132.5, 123.7, 118.9, 111.6, 110.1, 107.5, 106.3. EIMS (m/z, rel.int.); 235 (M$^+$, 100), 206 (10), 178 (15). Calcd for C$_{15}$H$_9$NO$_2$: C, 76.59; H, 3.86; N, 5.95. Found. C, 76.35; H, 3.88; N, 5.92.

4-(5′-Bromo-2,2′-bifuran-5-yl)-benzonitrile (4). The same procedure described for 2 was used starting with 3. Yield 65%, mp 127° C. $^1$H NMR (CDCl$_3$); δ 6.42 (d, J=3.6 Hz, 1H), 6.63 (d, J=3.6 Hz, 1H), 6.68 (d, J=3.6 Hz, 1H), 6.86 (d, J=3.6 Hz, 1H), 7.66 (d, J=8.4 Hz, 2H), 7.76 (d, J=8.4 Hz, 2H). $^{13}$C NMR (CDCl$_3$); δ 151.2, 147.6, 146.2, 134.0, 132.5, 124.0, 123.8, 122.3, 113.4, 110.4, 110.0, 108.4, 108.1. EIMS (m/z, rel.int.); 314 (M$^+$, 40), 234 (10), 206 (100). Calcd for C$_{15}$H$_8$BrNO$_2$: C, 57.32; H, 2.56; N, 4.46. Found. C, 56.93; H, 2.55; N, 4.39.

5′-(4-Cyanophenyl)-2,2′-bifuran-5-carbonitrile (5). A mixture of 4 (740 mg, 2.35 mmol) and Cu(I)CN (423 mg, 4.7 mmol) in dry DMF (25 mL) was refluxed for 48 h. The reaction mixture was poured onto water/ammonia and extracted with methylene chloride. The extract was washed with water and brine, dried over Na$_2$SO$_4$, then passed on silica gel to give analytically pure product 5 in 40% yield, mp 194-195° C. $^1$H NMR (DMSO-d$_6$); δ 7.17 (d, J=3.6 Hz, 1H), 7.21 (d, J=3.6 Hz, 1H), 7.43 (d, J=3.6 Hz, 1H), 7.76 (d, J=3.6 Hz, 1H), 7.91 (d, J=8.4 Hz, 2H), 7.99 (d, J=8.4 Hz, 2H). $^{13}$C NMR (DMSO-d$_6$); δ 152.3, 149.3, 144.3, 133.0, 132.9, 125.6, 124.3, 124.1, 118.7, 112.0, 111.8, 111.5, 110.0, 107.9.

EIMS (m/z, rel.int.); 260 (M⁺, 100), 231 (15), 203 (25), 177 (25), 140 (10), 130 (55). Calcd for $C_{16}H_8N_2O_2$: C, 73.84; H, 3.09; N, 10.76. Found. C, 73.62; H, 3.18; N, 10.92.

N-Hydroxy-5'-[4-(N-hydroxyamidino)-phenyl]-2,2'-bifuran-5-carboxamidine (6). A mixture of hydroxylamine hydrochloride (695 mg, 10 mmol, 10 eq.) in anhydrous DMSO (8 mL) was cooled to 5° C. under nitrogen and potassium t-butoxide (1120 mg, 10 mmol, 10 eq.) was added in portions. The mixture was stirred for 30 min. This mixture was added to the bis-cyano derivative 5 (260 mg, 1 mmol, 1 eq.). The reaction mixture was stirred overnight at room temperature. The reaction mixture was then poured slowly onto ice water (20 mL water and 20 mL ice). The precipitate was filtered and washed with water and then ethanol to afford 6 (free base) in 93% yield, mp 205-206° C. ¹H NMR (DMSO-d₆); δ 5.83 (br s, 4H), 6.86-6.89 (m, 3H), 7.14 (s, 1H), 7.75 (s, 4H), 9.70 (s, 1H), 9.75 (s, 1H). ¹³C NMR (DMSO-d₆); δ 152.3, 150.3, 146.7, 145.0, 144.9, 144.1, 132.3, 129.9, 125.8, 123.1, 109.7, 108.5, 107.2. EIMS (m/z, rel.int.); 327 (M⁺+1, 40), 307 (100), 299 (60), 273 (10), 220 (30). High resolution calcd for $C_{16}H_{15}N_4O_4$ ms 327.10933. Observed 327.11373.

N-Acetoxy-5'-[4-(N-acetoxyamidino)-phenyl]-2,2'-bifuran-5-carboxamidine (7). To a solution of 6 (262 mg, 0.8 mmol) in glacial acetic acid (8 mL) was slowly added acetic anhydride (0.28 mL). After stirring overnight, TLC indicated complete acylation of the starting material. The reaction mixture was poured onto ice water, the precipitate was filtered, washed with water and dried to give 7 in 89% yield, mp 212-213° C. ¹H NMR (DMSO-d₆); δ 2.17 (s, 6H), 6.85 (br s, 4H), 6.98 (d, J=3.6 Hz, 1H), 7.00 (d, J=3.6 Hz, 1H), 7.14 (d, J=3.6Hz, 1H), 7.24 (d, J=3.6 Hz, 1H), 7.79 (d, J=8.4 Hz, 2H), 7.87 (d, J=8.4 Hz, 2H). ¹³C NMR (DMSO-d₆); δ 168.4, 168.1, 155.8, 152.4, 148.9, 146.1, 144.8, 144.3, 131.2, 130.6, 127.2, 123.3, 113.1, 109.6, 109.3, 107.6, 19.8, 19.7. Calcd for $C_{20}H_{18}N_4O_6$: C, 58.53; H, 4.42. Found. C, 58.71; H, 4.50.

5'-(4-Amidinophenyl)-2,2'-bifuran-5-carboxamidine acetate salt (8a). To a solution of 7 (246 mg, 0.6 mmol) in glacial acetic acid (8 mL), and ethanol (20 mL) was added 10% palladium on carbon (60 mg). The mixture was placed in a Parr hydrogenation apparatus at 50 psi for 4 h at room temperature. The mixture was filtered through hyflo and the filter pad washed with water. The filtrate was evaporated under reduced pressure and the precipitate was collected and washed with ether to give 8a in 67% yield, mp 240-242° C. ¹H NMR (D₂O/DMSO-d₆); δ 1.80 (s, 2×CH₃), 7.06 (d, J=3.6 Hz, 1H), 7.11 (d, J=3.6 Hz, 1H), 7.36 (d, J=3.6 Hz, 1H), 7.39 (d, J=3.6 Hz, 1H), 7.89 (d, J=8.4 Hz, 2H), 7.98 (d, J=8.4 Hz, 2H). Calcd for $C_{16}H_{14}N_4O_2$-2.0AcOH-2.4H₂O: C, 52.48; H, 5.87; N, 12.23. Found. C, 52.28; H, 5.49; N, 11.91.

5'-(4-Amidinophenyl)-2,2'-bifuran-5-carboxamidine (8). The free base of 8a was prepared by dissolving the acetate salt (50 mg) in water (5 mL) and by neutralization with 1N NaOH. The precipitate was filtered, dried to afford free amidine 8, mp 202-203.5° C. ¹H NMR (DMSO-d₆); δ 6.93 (d, J=3.6 Hz, 1H), 7.01 (d, J=3.6 Hz, 1H), 7.11 (d, J=3.6 Hz, 1H), 7.7.22 (d, J=3.6 Hz, 1H), 7.83 (s, 4H). ¹³C NMR (DMSO-d₆); δ 162.2, 153.9, 152.4, 147.4, 145.7, 145.0, 134.1, 131.1, 127.3, 123.1, 111.9, 109.4, 109.2, 107.7. EIMS (m/z, rel.int.); 294 (M⁺, 50), 277 (100), 261 (25). High resolution mass calcd. for $C_{16}H_{14}N_4O_2$: 294.11168. Observed: 294.11013.

Example 2

6-(5'-Amidino-2,2'-bifuran-5-yl)-nicotinamidine

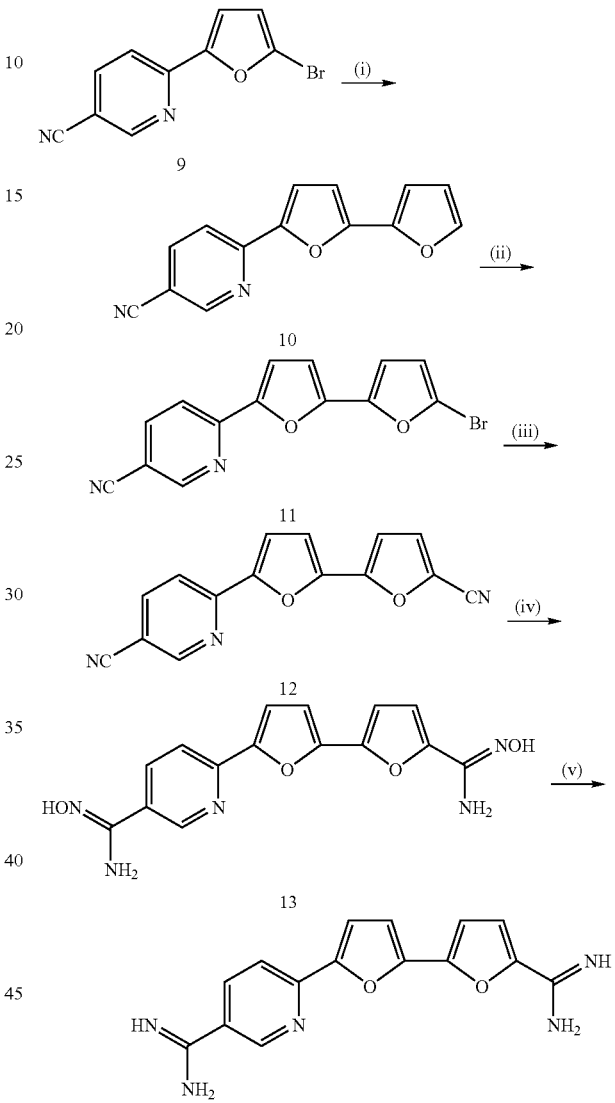

Reagents and conditions: (i) 2-tributyltin furan, Pd(PPh₃)₄; (ii) NBS, DMF; (iii) CuCN, DMF 110-120° C.; (iv) NH₂OH•HCl, KO-t-Bu, DMSO; (v) a) AcOH/Ac₂O; b) H₂/Pd—C, AcOH.

6-(2,2'-Bifuran-5-yl)-nicotinonitrile (10). Referring now to Scheme 3, the same procedure described for 3 was used starting with 9. Yield 78%, mp 169-170° C. ¹H NMR (CDCl₃); δ 6.52 (dd, J=3.6 Hz, J=1.8 Hz, 1H), 6.74 (m, 2H), 7.31 (d, J=3.6 Hz, 1H), 7.49 (d, J=1.8 Hz, 1H), 7.79 (d, J=8.4 Hz, 1H), 7.95 (dd, J=8.4, 2.1 Hz, 1H), 8.80 (d, J=2.1 Hz, 1H). ¹³C NMR; δ 152.5, 151.3, 151.0, 148.7, 145.5, 142.9, 139.6, 117.6, 117.0, 114.3, 111.7, 108.1, 107.1, 106.6. Calcd for $C_{14}H_8N_2O_2$: C, 71.18; H, 3.41; N, 11.85. Found. C, 70.83; H, 3.61; N, 11.84.

6-(5'-Bromo-2,2'-bifuran-5-yl)-nicotinonitrile (11). The same procedure described for 4 was used starting with 10. Yield 58%, mp 143-145° C. ¹H NMR (CDCl₃); δ 6.44 (d, J=3.6 Hz, 1H), 6.70 (d, J=3.6 Hz, 1H), 6.75 (d, J=3.6 Hz, 1H), 7.30 (d, J=3.6 Hz, 1H), 7.79 (d, J=8.4 Hz, 1H), 7.95 (dd, J=8.4, 2.1 Hz, 1H), 8.80 (d, J=2.1 Hz, 1H). $^{13}$C NMR; δ 152.5, 151.2, 151.1, 147.5, 147.3, 139.7, 122.8, 117.7, 117.0, 114.3, 113.5, 109.3, 108.6, 106.9. MS (m/z, rel.int.); 314 (M$^+$, 60), 285 (10), 235 (20), 207 (100), 179 (10). High resolution calcd for $C_{14}H_7BrN_2O_2$ ms 313.96909. Observed 313.96614.

6-(5'-Cyano-2,2'bifuran-5-yl)-nicotinonitrile (12). The same procedure described for 5 was used starting with 11. Yield 27%, mp 209-210.5° C. $^1$H NMR (DMSO-d$_6$); δ 7.23 (d, J=3.6 Hz, 1H), 7.27 (d, J=3.6 Hz, 1H), 7.52 (d, J=3.6 Hz, 1H), 7.79 (d, J=3.6 Hz, 1H), 8.04 (d, J=8.4 Hz, 1H), 8.39 (dd, J=8.4, 2.4 Hz, 1H), 9.03 (d, J=2.4 Hz, 1H). Anal. ($C_{15}H_7N_3O_2$) C, H.

N-Hydroxy-6-[5'-(N-hydroxyamidino)-2,2'-bifuran-5-yl]-nicotinamidine (13). The same procedure described for 6 was used starting with 12. Yield 89%, mp 248-250° C. $^1$H 8a. Yield 59%, mp 269-271° C. dec. $^1$H NMR (DMSO-d$_6$); δ 1.8 (s, 2×CH$_3$), 7.15 (d, J=3.6 Hz, 1H), 7.23 (d, J=3.6 Hz, 1H), 7.47 (d, J=3.6 Hz, 1H), 7.57 (d, J=3.6 Hz, 1H), 8.04 (d, J=8.4 Hz, 1H), 8.30 (d, J=8.4 Hz, 1H), 8.99 (s, 1H). MS (m/z, rel.int. thioglycerol); 296 (M$^+$+1, 100), 273 (12), 239 (40). High resolution calcd for $C_{15}H_{14}N_5O_2$ ms 296.1147. Observed 296.1189. Calcd for $C_{15}H_{13}N_5O_2$-2.0AcOH-2.65H$_2$O-0.5EtOH: C, 49.41; H, 6.07; N, 14.40. Found. C, 49.72; H, 5.96; N, 14.02.

Example 3

5,5'-bis-(4-N-Hydroxybenzamidine)-2,2'-bifuran (16) and 5,5'-bis-(4-Amidinophenyl)-2,2'-bifuran hydrochloride salt (17)

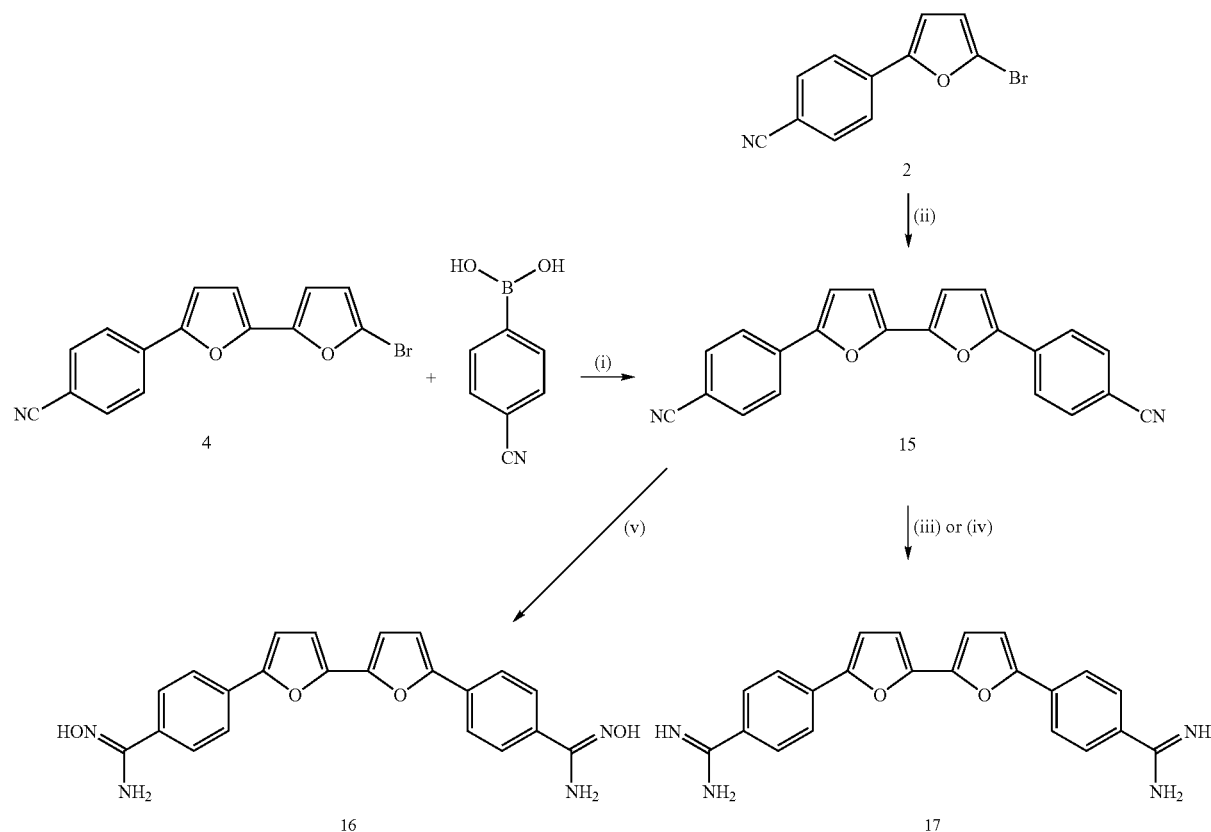

Scheme 4. Synthesis of 5,5'-bis-(4-N-Hydroxybenzamidine)-2,2'-bifuran (16) and 5,5'-bis-(4-Amidinophenyl)-2,2'-bifuran hydrochloride salt (17).

Reagents and conditions: (i) Pd(PPh$_3$)$_4$, Na$_2$CO$_3$, toluene, 80° C., 24 h; (ii) Bis(tributyltin), Pd(PPh$_3$)$_4$, toluene, 120° C., 4 h; (iii) a) LiN(TMS)$_2$, THF, r.t., overnight; b) HCl (gas), dry ethanol, r.t., overnight; (iv) a) HCl, EtOH; b) NH$_3$, EtOH; (v) NH$_2$OH•HCl, KO-t-Bu, DMSO, r.t., overnight.

NMR (DMSO-d$_6$); δ 5.88 (s, 2H), 6.04 (s, 2H), 6.92-6.96 (m, 3H), 7.29 (d, J=3.6 Hz, 1H), 7.84 (d, J=8.4 Hz, 1H), 8.11 (dd, J=8.4, 2.1 Hz, 1H), 8.88 (d, J=2.1 Hz, 1H), 9.80 (s, 1H), 9.92 (s, 1H). $^{13}$C NMR; δ 152.2, 148.7, 147.8, 147.0, 146.6, 146.0, 144.6, 144.0, 133.6, 127.3, 117.7, 111.3, 109.7, 108.5, 107.9. MS (m/z, rel.int.); 327 (M$^+$, 15), 311 (5), 295 (10), 278 (85), 261 (100). High resolution calcd for $C_{15}H_{13}N_5O_4$ ms 327.09675. Observed 327.09742.

6-(5'-Amidino-2,2'-bifuran-5-yl)-nicotinamidine acetate salt (14). Reduced using palladium on carbon analogously to 5,5'-bis-(4-Cyanophenyl)-2,2'-bifuran (15). Method (i): Referring now to Scheme 4, to a stirred solution of 4 (1.256 g, 4 mmol), and tetrakis(triphenylphosphine)palladium (230 mg) in toluene (8 mL) under a nitrogen atmosphere was added 4 mL of a 2 M aqueous solution of Na$_2$CO$_3$ followed by 4-cyanophenyl boronic acid (658 mg, 4.8 mmol) in 4 mL of methanol. The vigorously stirred mixture was warmed to 80° C. for 24 h, then cooled, and the precipitate was filtered. The precipitate was partitioned between methylene chloride (250 mL) and 2 M aqueous Na$_2$CO$_3$ (20 mL) containing 2.4 mL of concentrated ammonia. The organic layer was dried (Na$_2$SO$_4$), and then concentrated to dryness under reduced pressure to afford 15 in 52% yield; mp 298-299° C. (DMF). $^1$H NMR (DMSO-d$_6$); δ 7.09 (d, J=3.6 Hz, 2H), 7.39 (d, J=3.6 Hz, 2H), 7.89 (d, J=8.1 Hz, 4H), 7.97 (d, J=8.1 Hz, 4H). $^{13}$C NMR; δ 151.1, 145.8, 133.3, 132.7, 123.8, 118.6, 111.4, 109.45, 109.40. MS (m/z, rel.int.); 336 (M$^+$, 100), 307 (5), 279 (5), 206 (15), 168 (15). High resolution calcd for C$_{22}$H$_{12}$N$_2$O$_2$ ms 336.08988. Observed 336.08978. Calcd for C$_{22}$H$_{12}$N$_2$O$_2$-0.75H$_2$O: C, 75.52; H, 3.86; N, 8.00. Found. C, 75.12; H, 3.48; N, 7.74

Method (ii): Stille homocoupling using bis(n-tributyltin) as catalyst, similar to the Stille coupling described in the synthesis of 3, yield 78%.

5,5'-bis-(4-N-Hydroxybenzamidine)-2,2'-bifuran (16). The same procedure described for 6 was used starting with 15. Free base of 16, yield 82%; mp 309° C. dec. $^1$H NMR (DMSO-d$_6$); δ 5.86 (s, 4H), 6.97 (d, J=3.6 Hz, 2H), 7.17 (d, J=3.6 Hz, 2H), 7.76(d, J=8.4 Hz, 4H), 7.80 (d, J=8.4 Hz, 4H), 9.72 (s, 2H). $^{13}$C NMR; δ 152.3, 150.3, 145.2, 132.3, 129.9, 125.8, 123.1, 108.6, 108.5. MS (m/z, rel.int.); 403 (M$^+$+1, 90), 388 (15), 370 (10), 201 (100). Hydrochloride salt of 16. mp>320° C.dec. Calcd for C$_{22}$H$_{18}$N$_4$O$_4$-2.0HCl-1.0H$_2$O: C, 53.56; H, 4.49; N, 14.37; Cl, 14.37. Found C, 53.52; H, 4.40; N, 11.00; Cl, 14.13.

5,5'-bis-(4-Amidinophenyl)-2,2'-bifuran hydrochloride salt (17). Method (iii): Prepared by using Li-amide method in 90% yield, starting with 15. The dinitrile 15 (1.67 mmol), suspended in freshly distilled THF (5 mL), was treated with lithium trimethylsilylamide (2% solution in THF, 3.67 mmol) and the reaction was stirred overnight. The reaction mixture was then cooled to 0° C. and HCl (g) saturated ethanol was added whereupon a precipitate started forming. The reaction was left to run overnight, whereafter it was diluted with ether and the formed solid was filtered to give the diamidine salt. Method (iv): Prepared from 15 by using the Pinner method. See Das, B. P. and D. W. Boykin, *J. Med. Chem.*, 20, 531-536 (1977); McFarland, J. W. and H. L. Howes, Jr., *J. Med. Chem.*, 15, 365-368 (1972). Yield 30%, mp 325-327.5° C. dec. $^1$H NMR (DMSO-d$_6$); δ 7.16 (d, J=3.6 Hz, 2H), 7.47 (d, J=3.6 Hz, 2H), 7.96 (d, J=8.4 Hz, 4H), 8.05 (d, J=8.4 Hz, 4H), 9.17 (s, 2H), 9.45 (s, 2H). $^{13}$C NMR; δ 164.7, 151.4, 145.9, 134.1, 129.0, 126.3, 123.5, 111.4, 109.5. MS (m/z, rel.int.); 371 (8), 337 (50), 201 (100). Calcd for C$_{22}$H$_{18}$N$_4$O$_2$-2.0HCl-1.0H$_2$O: C, 57.28; H, 4.75; N, 12.03. Found C, 57.56; H, 4.75; N, 12.03.

Example 4

5,5'-Bis-[4-(N-methoxyamidino)phenyl]-2,2'-bifuran Maleate (19)

Scheme 5. Synthesis of 5,5'-Bis-[4-(N-methoxyamidino)phenyl]-2,2'-bifuran Maleate (19).

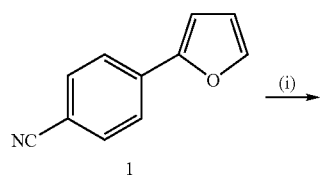

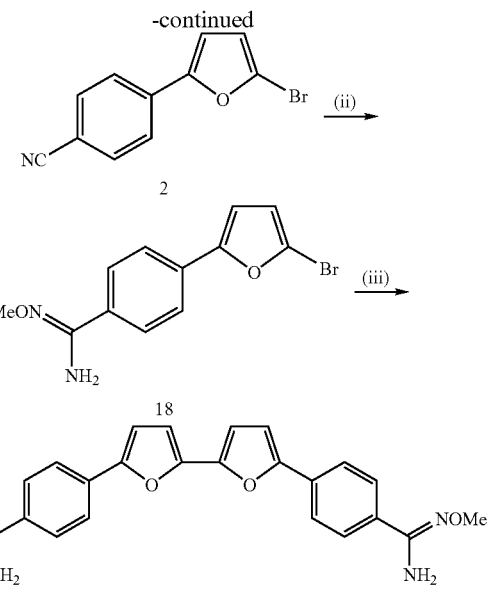

Reagents and conditions: (i) NBS, DMF; (ii) a) NH$_2$OH•HCl, KO-t-Bu, DMSO; b) LiOH, (Me)$_2$SO$_4$, dioxane/DMSO; (iii) (Bu$_3$Sn)$_2$, Pd(PPh$_3$)$_4$, toluene, 120° C., 3 h.

2-Bromo-5-(4-cyanophenyl)furan (2). Referring now to Scheme 5 above, to a chilled (ice/water bath) solution of 2-(4-cyanophenyl)furan (28.25 g, 0.167 mol) in DMF (100 ml) was added portionwise NBS (31.20 g, 1.05 eq., freshly recrystallized from nitromethane) with stirring (approximately 1 g portions over course of approximately 40 minutes). The resulting solution was stirred for 2 h at room-temperature, at which point TLC showed consumption of starting material. During the course of the reaction, the color went from yellow to orange and then finally to red. The solution was then diluted with water (approximately 300 ml) to give a pink/red solid, which was collected, washed with water, and air dried. Yield: 39.0 g, 94%. A small sample was recrystallized from MeOH/water to give a pale red crystalline solid, mp 96.5-97° C. $^1$H NMR (DMSO-d$_6$): 6.80 (d, J=3.6 Hz, 1H), 7.29 (d, J=3.6 Hz, 1H), 7.87 (m, 4H). IR (cm$^{-1}$): 3142, 3128, 3060, 2226, 1613, 1515, 1475, 1015, 929, 833, 787, 545.

2-Bromo-5-[4-(N-methoxyamidino)phenyl]furan (18). To a chilled suspension of hydroxylamine hydrochloride (17.25 g, 0.25 mol) in DMSO (150 ml) was added portionwise KO-t-Bu (28.0 g, 0.25 mol) and the mixture was stirred under nitrogen for 30 min. 2-Bromo-5-(4-cyanophenyl)furan (17.37 g, 0.07 mol) was then added and the mixture was stirred overnight at room-temperature. The resulting solution was diluted with excess water to give 2-bromo-5-[4-(N-hydroxyamidino)phenyl]furan as an off-white solid, which was collected and washed with water. Yield: 19.45 g, 99%; mp 162-164° C. $^1$H NMR (DMSO-d$_6$): 5.84 (broad s, 2H), 6.71 (d, J=3.6 Hz, 1H), 7.05 (d, J=3.6 Hz, 1H), 7.65 (d, J=8.4 Hz, 2H), 7.72 (d, J=8.4 Hz, 2H), 9.70 (s, 1H). IR (cm$^{-1}$): 3475, 3369, 3209 (broad), 1639, 1482, 1341, 1017, 927, 787. The intermediate amidoxime (38.9 g, 0.138 mol) was dissolved in a mixture of DMSO (60 ml) and dioxane (300 ml) and with chilling was treated with a solution of LiOH hydrate (11.61 g, 0.277 mol) in water (60 ml). At room temperature, the resulting suspension was then treated dropwise via an addition funnel with dimethyl sulfate (26.18 g. 0.208 mol) over the course of ~30 min. Following the addition, the mixture became slightly warm and the solids dissolved. After stirring overnight, the mixture was diluted with excess water and extracted with EtOAc. Purification of the residue by column chromatography on silica gel eluting with 10% EtOAc in hexane gave the slightly impure product, which was further purified by recrystallization from MeOH/water in multiple crops to give an off-white solid, mp 116-117° C. Yield: 28.0 g, 69%. $^1$H NMR (DMSO-d$_6$, an apparent mixture of stereoisomers): 3.74 (2s, 3H), 6.09 (broad s, 2H), 6.72 (2d, J=3.6 Hz, 1H), 7.09 (2d, J=3.6 Hz, 1H), 7.70 (m, 4H). IR (cm$^{-1}$): 3459, 3312, 3177, 2957, 2935, 2901, 2818, 1634, 1403, 1051, 910, 842, 785.

5,5'-Bis-[4-(N-methoxyamidino)phenyl]-2,2'-bifuran (19). A mixture of 2-bromo-5-[4-(N-methoxyamidino)phenyl]furan (27.90 g, 94.5 mmol), hexa-n-butyiditin (28.37 g, 48.9 mmol) and tetrakis(triphenylphosphine)palladium(0) (1.40 g, 1.2 mmol) in toluene (400 ml) was heated under nitrogen in an oil bath set at 120° C. for 3 h and then cooled to room temperature. After standing 1 h, the resulting precipitate was collected and rinsed with diethyl ether to give a yellow fluffy solid (12.25 g, 60%). The product was recrystallized by being dissolved in hot DMF (100 ml) and then adding MeOH (200 ml). After chilling for several hours, the product was collected and rinsed with MeOH to yield a fine yellow crystalline solid, mp 258-259° C. Yield: 10.75 g, 53%. $^1$H NMR (DMSO-d$_6$): 3.76 (s, 6H), 6.11 (br s, 4H), 6.99 (d, J=3.6 Hz, 2H), 7.20 (d, J=3.6 Hz, 2H), 7.73 (d, J=8.7 Hz, 4H), 7.80 (d, J=8.7 Hz, 4H). $^{13}$C NMR (DMSO-d$_6$): 60.6, 108.5, 108.8, 123.1, 126.2, 130.3, 131.4, 145.2, 150.5, 152.2. IR (cm$^{-1}$): 3520, 3412, 3125, 2991, 2961, 2897, 2817, 1622, 1415, 1402, 1056, 904, 842, 789. MS (EI): m/z 431 (MH$^+$). Anal. Calcd. for C$_{24}$H$_{22}$N$_4$O$_4$ (430.46): C, 66.96; H, 5.15; N, 13.02. Found: C, 66.91; H, 5.14; N, 13.01.

5,5'-Bis-[4-(N-methoxyamidino)phenyl]-2,2'-bifuran Maleate (19a). The free base (8.61 g, 20.0 mmol) and maleic acid (2.33 g, 20.0 mmol) were heated overnight in EtOH (200 ml) at 50-60° C. and then at reflux for 30 min. The suspension was then concentrated in vacuo, and the residue was triturated with diethyl ether, filtered and vacuum dried at 50-60° C. for 24 hr to give a fluffy yellow solid (10.50 g). Combustion analysis showed that only 0.8 molar equivalent of maleic acid was present in the product. $^1$H NMR (DMSO-d$_6$): 3.76 (s, 6H), 6.23 (broad s) and 6.24 (s): maleate vinyl Hs overlapping with 2NH$_2$, integration 0.83% of expected, 6.99 (d, J=3.6 Hz, 2H), 7.21 (d, J=3.6 Hz, 2H), 7.74 (d, J=8.7 Hz, 4H), 7.82 (d, J=8.7 Hz, 4H). Calcd. for C$_{24}$H$_{22}$N$_4$O$_4$·0.8C$_4$H$_4$O$_4$ (523.32): C, 62.42; H, 4.85; N, 10.71. Found: C, 62.72; H, 4.94; N, 10.74.

Example 5

5,5'-Bis-(5-amidino-2-pyridyl)-2,2'-bifuran (22) and 5,5'-Bis-[5-(N-methyoxyamidino)-2-pyridyl]-2,2'-bifuran (23)

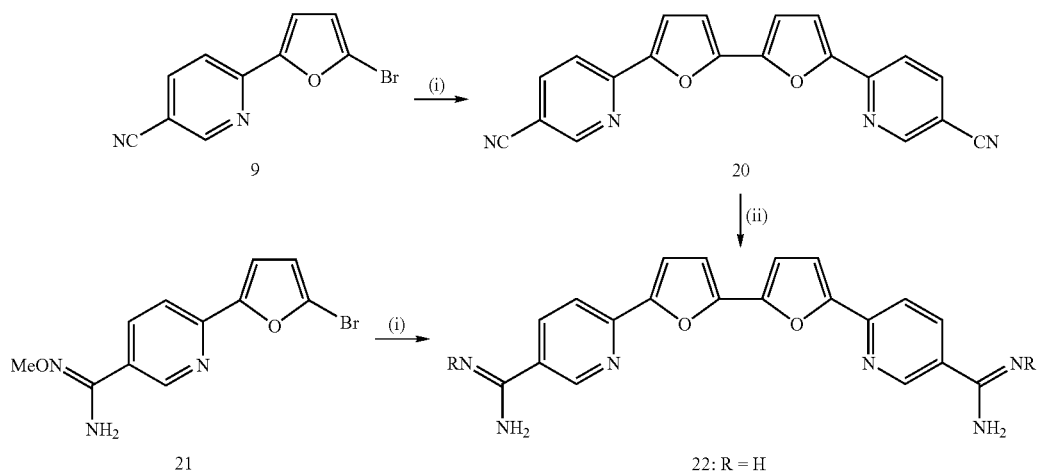

Scheme 6. Synthesis of Compounds 22 and 23.

22: R = H
23: R = OMe

Reagents and conditions: (i) Bis(tributyltin), Pd(PPh$_3$)$_4$, toluene, 120° C., 4 h; (ii) a) LiN(TMS)$_2$, THF, r.t., overnight; b) HCl (gas), dry ethanol, r.t., overnight.

Compound 20. Referring now to Scheme 6 above, compound 20 was prepared via Stille homocoupling of 9, analogously to the synthesis of 15 from 2. Yield 81%, mp>300° C. $^1$H NMR (DMSO-d$_6$); δ 7.17 (d, J=3.6 Hz, 2H), 7.48 (d, J=3.6 Hz, 2H), 8.00 (d, J=8.1 Hz, 2H), 8.31 (dd, J=8.1, 2.1 Hz, 2H), 8.98 (d, J=2.1 Hz, 2H). $^{13}$C NMR; δ 152.3, 151.5, 149.9, 146.5, 140.3, 117.9, 116.6, 114.2, 110.1, 106.4. MS (m/z, rel.int.); 339 (M$^+$+1, 100), 319 (15), 277 (10).

5,5'-Bis-(5-amidino-2-pyridyl)-2,2'-bifuran (22). Nitrile reduction using LiN(TMS)$_2$ analogous to 17. Yield 92%, mp>300° C. $^1$H NMR (D$_2$O/DMSO-d$_6$); δ 7.21 (d, J=3.6 Hz, 2H), 7.52 (d, J=3.6 Hz, 2H), 8.07 (d, J=8.4 Hz, 2H), 8.31 (dd, J=8.4, 2.1 Hz, 2H), 9.00 (d, J=2.1 Hz, 2H). $^{13}$C NMR; δ 164.1, 152.2, 151.9, 149.3, 147.3, 137.7, 122.5, 118.8, 114.9, 110.9. MS (m/z, rel.int.); 373 (M$^+$+1, 60), 356 (5), 187 (100). Calcd for C$_2$H$_{16}$N$_6$O$_2$·4.0HCl·0.75H$_2$O: C, 45.17; H, 4.08; N, 15.80. Found C, 45.17; H, 4.25; N, 15.53.

5,5'-Bis-[5-(N-methyoxyamidino)-2-pyridyl]-2,2'-bifuran (23). Stille homocoupling analogous to 19. Free base yield 95%, mp>292-294° C. $^1$H NMR (DMSO-d$_6$); δ 3.80 (s, 6H), 6.07 (s, 4H), 7.06 (d, J=3.6 Hz, 2H), 7.30 (d, J=3.6 Hz, 2H), 7.85 (d, J=8.4 Hz, 2H), 8.11 (d, J=8.4 Hz, 2H), 8.88 (s, 2H). $^{13}$C NMR; δ 152.4, 148.8, 148.0, 146.7, 145.8, 133.7, 126.4, 117.5, 111.3, 109.0, 60.4. MS (m/z, rel.int.); 432 (M$^+$, 100), 385 (20), 370 (60).

Hydrochloride salt of 23: mp 254-256° C. Calcd for $C_{22}H_{20}N_6O_4 \cdot 4.0HCl \cdot 2.5H_2O$: C, 42.39; H, 4.68; N, 13.48. Found C, 42.32; H, 4.52; N, 13.35.

Example 6

5,5'-Bis-(4-amidinophenyl)-2,2'-bithiophene (26a) and 5,5'-Bis-(4-amidino-2-Pyridyl)-2,2'-bithiophene (26b)

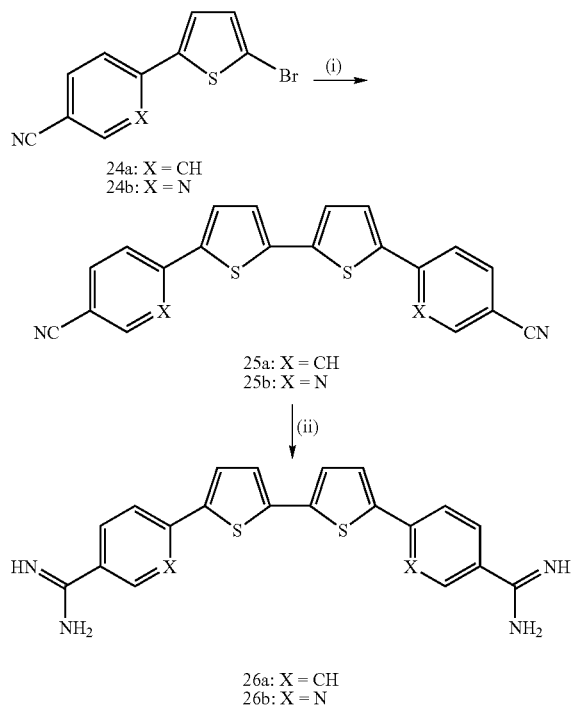

Scheme 7. Synthesis of compounds 26a and 26b.

Reagents and conditions: (i) Bis(tributyltin), Pd(PPh$_3$)$_4$, toluene, 120° C., 4 h; (ii) a) LiN(TMS)$_2$, THF, r.t., overnight; b) HCl (gas), dry ethanol, r.t., overnight.

Compound 25a. Referring now to Scheme 7, 25a was prepared via Stille homocoupling of 24a. Yield 91%, mp 298-300° C. $^1$H NMR(DMSO-d$_6$); δ 7.45 (d, J=4.2 Hz, 2H), 7.68 (d, J=4.2 Hz, 2H), 7.85-7.89 (m, 8H). $^{13}$C NMR; δ 140.3, 137.0, 132.5, 126.8, 125.7, 125.4, 118.0, 109.6. Calcd for $C_{22}H_{12}N_2S_2$: C, 71.71; H, 3.28. Found C, 71.48; H, 3.40.

Compound 25b. Prepared via Stille homocoupling of 24b. Yield 85%, mp 300° C. $^1$H NMR (DMSO-d$_6$); δ 7.53 (d, J=4.2 Hz, 2H), 7.94 (d, J=4.2 Hz, 2H), 8.07 (d, J=8.1 Hz, 2H), 8.23 (d, J=8.1 Hz, 2H), 8.90 (s, 2H). MS (m/z, rel.int.); 370 (M$^+$, 100), 337 (30), 305 (5), 292 (5), 223 (20), 185 (60), 163 (80). Calcd for $C_{20}H_{10}N_4S_2$: C, 64.84; H, 2.72. Found C, 64.59; H, 2.88.

5,5'-Bis-(4-amidinophenyl)-2,2'-bithiophene (26a). Nitrile reduction of 25a using LiN(TMS)$_2$. Yield 73%, mp>300° C. $^1$H NMR(D$_2$O/DMSO-d$_6$); δ 7.52 (d, J=3.9 Hz, 2H), 7.75 (d, J=3.9 Hz, 2H), 7.88 (d, J=8.4 Hz, 4H), 7.94 (d, J=8.4 Hz, 4H). $^{13}$C NMR; δ 165.6, 141.3, 138.8, 137.8, 129.4, 127.7, 126.7, 126.0. MS (m/z, rel.int.); 403 (M$^+$+1, 20), 386 (25), 368 (40), 185 (95), 171 (100). Calcd for $C_{22}H_{18}N_4S_2 \cdot 2.0HCl \cdot 2.4H_2O$: C, 51.05; H, 4.79; N, 10.80. Found C, 51.12; H, 4.57; N, 10.50.

5,5'-Bis-(4-amidino-2-pyridyl)-2,2'-bithiophene (26b). Nitrile reduction of 25b using LiN(TMS)$_2$. Yield 89%, mp>300° C. $^1$H NMR (D$_2$O/DMSO-d$_6$); δ 7.55 (d, J=3.9 Hz, 2H), 7.94 (d, J=3.9 Hz, 2H), 8.09 (d, J=8.4 Hz, 2H), 8.24 (dd, J=8.4, 2.1 Hz, 2H), 8.93 (d, J=2.1 Hz, 2H). MS (m/z, rel.int.); 405 (M$^+$+1, 50), 231 (15), 203 (100). Calcd for $C_{20}H_{16}N_6S_2 \cdot 4.0HC_2 \cdot 0.75H_2O$: C, 42.60; H, 3.84; N, 14.90. Found C, 42.56; H, 3.83; N, 14.66.

Example 7

5,5'-Bis-(4-amidinophenyl)-2,2'-biselenophene (29a) and 5,5'-Bis-(4-amidino-2-pyridyl)-2,2'-biselenophene (29b)

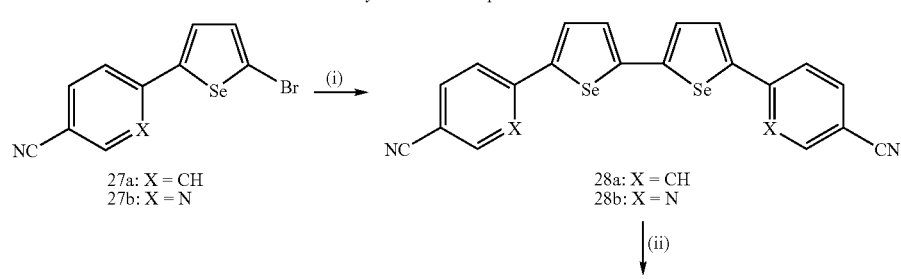

Scheme 8. Synthesis of Compounds 29a and 29b.

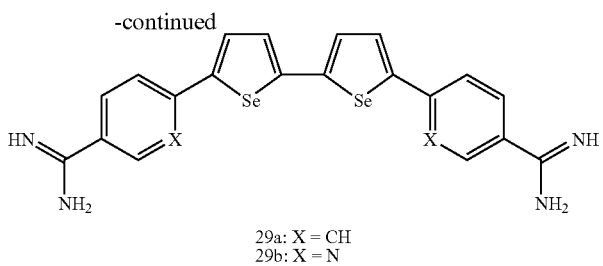

29a: X = CH
29b: X = N

Reagents and conditions: (i) Bis(tributyltin), Pd(PPh₃)₄, toluene, 120° C., 4 h; (ii) a) Lin(TMS)₂, THF, r.t., overnight; b) HCl (gas), dry ethanol, r.t., overnight.

Compound 28a. Referring to Scheme 8 above, Stille homocoupling of 27a gave 28a. Yield 92%, mp 285-286.5° C. $^1$H NMR(DMSO-d₆); δ 7.52 (d, J=3.9 Hz, 2H), 7.76-7.84 (m, 10H). $^{13}$C NMR; δ 146.6, 144.5, 139.2, 132.6, 129.1, 128.6, 125.9, 118.2, 109.6. MS (m/z, rel.int.); 462 (M⁺, 90), 464 (M⁺+2, 100), 384 (5), 302 (15). Calcd for C₂₂H₁₂N₂Se₂: C, 57.16; H, 2.62. Found C, 56.98; H, 2.63.

Compound 28b. Stille homocoupling of 27b. Yield 85%, mp>300° C. $^1$H NMR (DMSO-d₆); δ 1.62 (d, J=3.9 Hz, 2H), 7.98-8.30 (m, 6H), 8.93 (d, J=2.1 Hz, 2H). MS (m/z, rel.int.); 464 (M⁺, 60), 466 (M⁺+2, 100), 385 (25), 305 (40).

5,5'-Bis-(4-amidinophenyl)-2,2'-biselenophene (29a). Nitrile reduction of 28a analogous to preparation of 17. Yield 80%, mp>300° C. $^1$H NMR (D₂O/DMSO-d₆); δ 7.46 (d, J=3.9 Hz, 2H), 7.72-7.82 (m, 10H). $^{13}$C NMR; δ 165.4, 147.4, 145.1, 140.6, 129.5, 129.3, 129.2, 126.9, 126.3. MS (m/z, rel.int.); 496 (M⁺, 10), 498 (M⁺+2, 20), 250 (100). Calcd for C₂₂H₁₈N₄Se₂·2.0HCl·1.5H₂O: C, 44.31; H, 3.90; N, 9.36. Found C, 44.28; H, 3.90; N, 9.13.

5,5'-Bis-(4-amidino-2-pyridyl)-2,2'-biselenophene (29b). Nitrile reduction of 28b analogous to the preparation of 17. Yield 71%, mp>300° C. $^1$H NMR (D₂O/DMSO-d₆); δ 7.50 (s, 2H), 7.91-8.09 (m, 6H), 8.77 (s, 2H). MS (m/z, rel.int.); 499 (M⁺+1, 25), 484 (15), 290 (30), 251 (100). Calcd for C₂₀H₁₆N₆Se₂·3.0HCl·0.4EtOH: C, 39.90; H, 3.41; N, 13.40. Found C, 39.98; H, 3.19; N, 13.07.

Example 8

Compounds 32 and 33

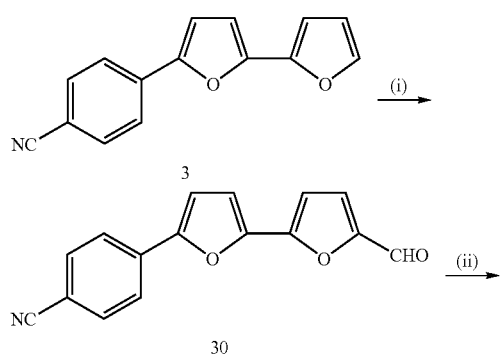

Scheme 9. Synthesis of Compounds 32 and 33.

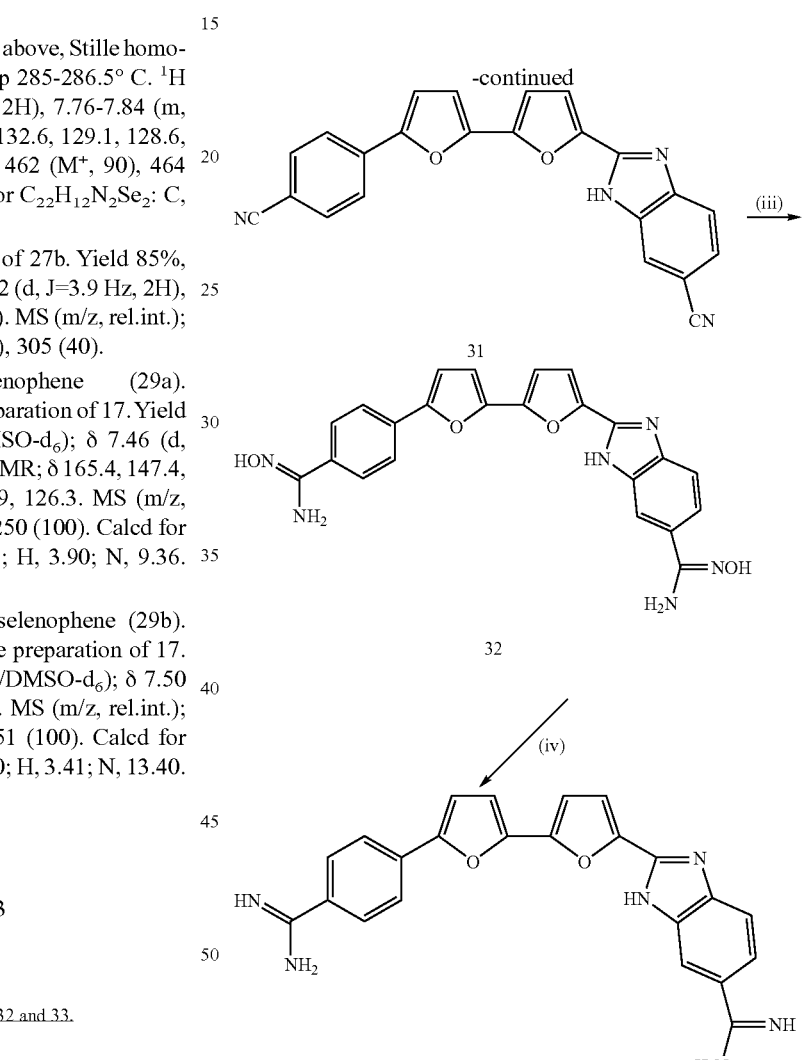

Reagents and conditions: (i) DMF/POCl₃; (ii) 3,4-diaminobenzonitrile, 1,4-benzoquinone;
(iii) NH₂OH·HCl, KO-t-Bu, DMSO; (iv) a) AcOH/Ac₂O; b) H₂/Pd—C, AcOH.

Compound 30. Referring to Scheme 9 above, freshly distilled DMF (4.2 mL) was stirred in an ice bath and treated dropwise with POCl₃ (14 mL) and then portionwise 3 (1.645 g, 7 mmol) in methylene chloride (12 mL) was added. The reaction mixture was stirred under heating at 60° C. for 2 h. The methylene chloride was distilled off under reduced pressure, then the remaining solution was poured into ice water and the product was extracted into EtOAc. The extract was dried and evaporated to give 30 in 85.7%, mp 176° C. $^1$H NMR (CDCl$_3$); δ 6.86 (d, J=3.9 Hz, 1H), 6.95 (d, J=3.6 Hz, 1H), 7.03 (d, J=3.6 Hz, 1H), 7.35 (d, J=3.9 Hz, 1H), 7.70 (d, J=8.4 Hz, 2H), 7.82 (d, J=8.4 Hz, 2H), 9.66 (s, 1H). $^3$C NMR; δ 176.9, 153.1, 151.9, 150.4, 145.5, 133.5, 132.6, 124.2, 123.3, 118.6, 111.9, 111.1, 110.4, 108.2. Calcd for C$_{16}$H$_9$NO$_3$: C, 73.00; H, 3.44; N, 5.32. Found. C, 73.09; H, 3.58; N, 5.25.

Compound 31. A solution of 30 (526 mg, 2 mmol), 3,4-diaminobenzonitrile (266 mg, 2 mmol), and benzoquinone (216 mg, 2 mmol) in ethanol (25 mL) was allowed to reflux under nitrogen for overnight. The reaction mixture was distilled under reduced pressure. The residue was triturated with ether and filtered to afford 31 in 79.7%, mp 295-296° C. $^1$H NMR (DMSO-d$_6$); δ 7.10 (d, J=3.6 Hz, 1H), 7.17 (d, J=3.6 Hz, 1H), 7.44 (d, J=3.6 Hz, 2H), 7.62 (d, J=7.2 Hz, 1H), 7.69 (d, J=7.5 Hz, 0.5H), 7.80 (d, J=7.2 Hz, 0.5H), 8.18 (s, 1H), 13.58 (s, 1H). $^{13}$C NMR (DMSO-d$_6$); δ 151.5, 146.6, 145.6, 144.2, 133.3, 132.9, 124.0, 119.9, 118.8, 114.3, 111.6, 110.1, 109.6, 109.3, 104.2. EIMS (m/z, rel.int.); 376 (M$^+$, 100), 319 (5), 246 (10), 218 (10), 188 (15). High resolution calcd for C$_{23}$H$_{12}$N$_4$O$_2$ ms 376.09603. Observed 376.09468. Anal. Calcd for C$_{23}$H$_{12}$N$_4$O$_2$: C, 73.39; H, 3.21; N, 14.88. Found. C, 73.12; H, 3.23; N, 14.87.

Compound 32. Analogous to the preparation of 6, starting with 31. Yield 93%, mp>300° C. $^1$H NMR (DMSO-d$_6$); δ 5.86 (s, 2H), 6.20 (s, 2H), 7.02-7.17 (m, 2H), 7.19 (d, J=3.6 Hz, 1H), 7.37 (d, J=3.6 Hz, 1H), 7.58 (s, 2H), 7.76-7.97 (m, 5H), 9.66 (s, 2H), 13.00 (br s, 1H). EIMS (m/z, rel.int.); 443 (M$^+$+1, 60), 428 (25), 241 (20), 222 (100).

Compound 33. Analogous to the preparation of 14, starting with 32. Yield 67%, mp 248-250° C. $^1$H NMR (D$_2$O/DMSO-d$_6$); δ 1.87 (s, 3×CH$_3$), 7.15 (s, 2H), 7.32-7.46 (m, 2H), 7.66-7.79 (m, 2H), 7.95-8.24 (m, 5H). MS (m/z, rel.int.); 410 (M$^+$, 10), 392 (100), 365 (90), 350 (80), 336 (5). Calcd for C$_{23}$H$_{18}$N$_6$O$_2$·3.0AcOH·0.35H$_2$O: C, 58.35; H, 5.14; N, 14.09. Found. C, 58.03; H, 4.88; N, 14.20.

Example 9

Compound 39

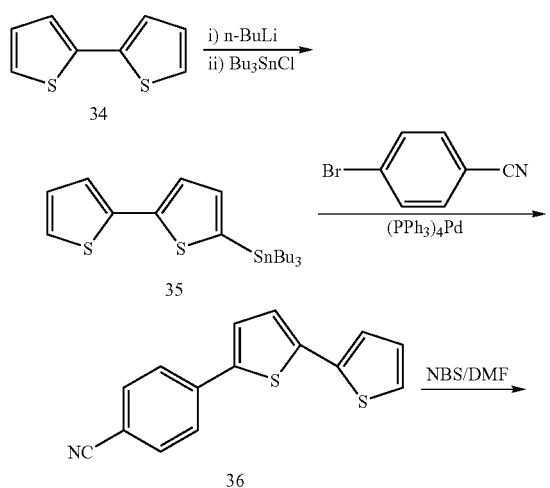

Scheme 10. Synthesis of Compound 39.

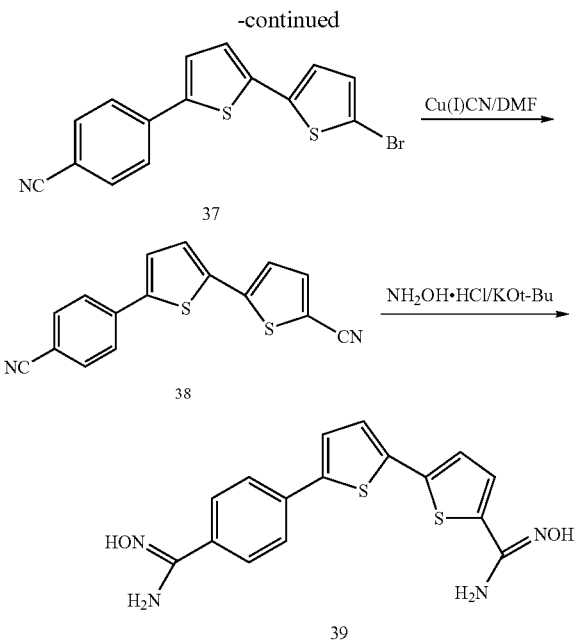

Example 10

Compound 45

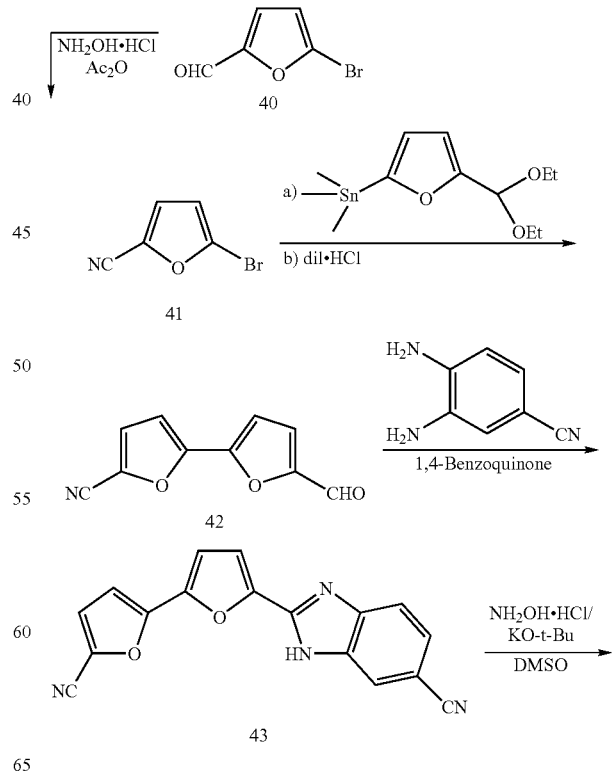

Scheme 11. Synthesis of Compound 45

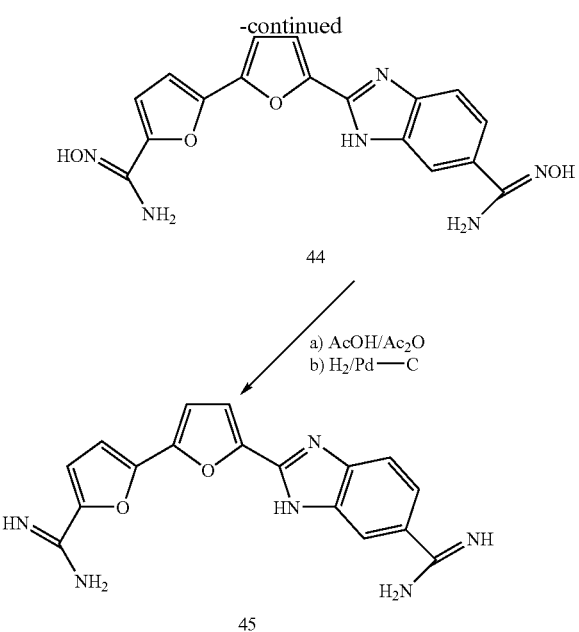

44

Example 11

Measurement of ΔTm of Novel Bichalcophenes

DNA binding studies with polyA.polyT were carried out using established protocols. See Wilson, W. D., et al., *Biochemistry*, 32, 4098-4104 (1993). The increase in thermal melting (ΔTm) of polyA.polyT in the presence of compounds 8, 14, 17, and 45, as well as of furamidine and pentamidine are shown below in Table 1.

Example 12

In Vitro Antiprotozoan Activity of Novel Bichalcophenes

In vitro antiprotozoal activities were measured following established protocols. See Ismail, M. A., et al., *J. Med. Chem.*, 46, 4761-4769 (2003); Stephens, C. E., et al., *Bioorg. Med. Chem. Lett.*, 13, 2065-2069 (2003) (in vitro assay against *Leishmania donovani*). The activities of compounds 8, 14, 16, 17, 19, 22, 26a, 26b, 29a, 29b, and 33, 39, and 45 against *Trypanosoma brucei riodesiense* (T. b. r.), *Plasmodium falciparum* (P. f.), *Leishmania donovani* (L. d.), and L-6 rat mycoblast cells (as an assay for cell toxicity) are shown in Table 1. These values are compared to those of pentamidine and furamidine.

Five compounds, 8, 14, 26a, 29a, and 33, had $IC_{50}$ values for T. b. r. that were 26 nM or less. Four compounds, 14, 17, 26a, and 29a, had $IC_{50}$ values for P. f. that were 22 nM or below. Three of the compounds 17, 26a, and 29a, had $IC_{50}$ values for L. d. that were 1 μM, less than the 2.0 μM and 2.3 μM $IC_{50}$ values exhibited by pentamidine and furamidine, respectively. As expected, the prodrugs, 6, 16, and 19, exhibited poor in vitro activity due to the absence of the enzymes needed for bioconversion to the active diamidines.

Example 13

In Vivo Antiprotozoan Activity of Novel Bichalcophenes

The activities of compounds 6, 8, 14, 16 and 17, against the STIB 900 strain of *Trypanosoma brucei rhodesiense* (T. b. r.) in a mouse model are shown in Table 2. These values are compared to those of pentamidine and furamidine. Groups of four mice were infected intraperitoneally with 2×105 bloodstream forms of T. b. r. STIB 900 which originates from a patient in Tanzania. On days 3, 4, 5, and 6 post-infection the experimental groups were treated with the drugs either by the intraperitoneal or for prodrugs by the oral route. Usually the highest tolerated dose was used which was determined in a pretoxicological experiment. Parasitemia of the mice was checked daily up to day 14 post-infection and thereafter 2 times per week up to day 60. One group of mice was not treated and acted as control. For relapsing mice, the day of death was recorded and the survival time determined.

Compounds 8 and 14 show good in vivo activity against T. b. r. in the murine model. Both compounds exhibited better cure rates than pentamidine and furamidine. The best cure rate, three mice out of four, was seen with 14, despite a dosage of half that of furamidine and pentamidine.

TABLE 1

In Vitro Activity of Antiprotozoan Dicationic Bichalcophenes.

| Code | X | R | $R_1$ | Δ Tm | T.b.r. $IC_{50}$ (nM) | P.f. $IC_{50}$ (nM) | L.d. $C_{50}$ (μM) | L6 Rat Mycoblast Cells $IC_{50}$ (μM) |
|---|---|---|---|---|---|---|---|---|
| Pentamidine | NA | NA | NA | 12.6 | 2.2 | NT | 2.0 | 11.4 |
| Furamidine | NA | | | 25 | 4.5 | 15.5 | 2.3 | 6.4 |
| 8 | O | PhAm | Am | 10.8 | 12 | 41.5 | NT | 37.8 |
| 39 | S | PhAmOH | AmOH | | 45.5 K | 1.39 K | NT | >203 |
| 14 | O | PyAm | Am | 7.1 | 9.7 | 6 | NT | 26.9 |
| 17 | O | PhAm | PhAm | 23.6 | 126 | 20 | 1.0 | 10.7 |
| 16 | O | PhAmOH | PhAmOH | | 8.7 K | 2.96 K | NT | >182 |
| 19 | O | PhAmM | PhAmM | | 36 K | >7.4 K | NT | >133 |
| 22 | O | PyAm | PyAm | | 70 | 29 | >100 | 5.1 |
| 26a | S | PhAm | PhAm | | 15 | 22 | 0.289 | 89.4 |

TABLE 1-continued

In Vitro Activity of Antiprotozoan Dicationic Bichalcophenes.

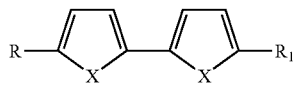

| Code | X | R | R$_1$ | Δ Tm | T.b.r. IC$_{50}$ (nM) | P.f. IC$_{50}$ (nM) | L.d. C$_{50}$ (μM) | L6 Rat Mycoblast Cells IC$_{50}$ (μM) |
|---|---|---|---|---|---|---|---|---|
| 26b | S | PyAm | PyAm | | 36 | 34 | >50 | >159 |
| 29a | Se | PhAm | PhAm | | 26 | 14 | 0.12 | 13.4 |
| 29b | Se | PyAm | PhAm | | 153 | 76 | 19.8 | >144 |
| 45 | O | ImAm | Am | 23.2 | 102 | 92 | | 41.8 |
| 33 | O | ImAm | PhAm | | 15 | 37 | >100 | 56.1 |

R and R$_1$:

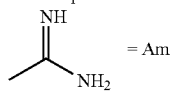 = Am

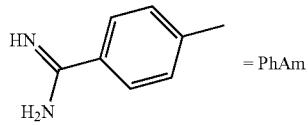 = PhAm

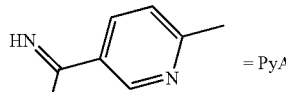 = PyAm

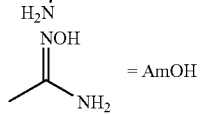 = AmOH

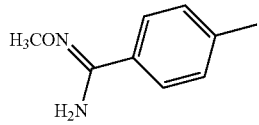 = PhAmOH

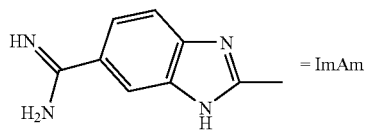 = PhAmM

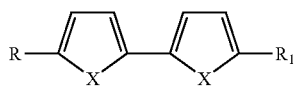 = ImAm

TABLE 2

In Vivo T.b.r. Activity of Antiprotozoan Dicationic Bichalcophenes.

| Code | X | R | R$_1$ | Dosage route$^a$ | Dosage (mg/kg) | Cures$^b$ | Survival (days)$^c$ |
|---|---|---|---|---|---|---|---|
| Pentamidine | NA | NA | NA | ip | 20 | 0/4 | >42.75 |
| Furamidine | NA | NA | NA | ip | 20 | 0/4 | >52.5 |
| 6 | O | PhAmOH | AmOH | po | 75 | 0/4 | 20 |
| 8 | O | PhAm | Am | ip | 20 | 2/4 | >45.5 |
| 14 | O | PyAm | Am | ip | 10 | 3/4 | >51.25 |
| 17 | O | PhAm | PhAm | ip | 10 | 0/4 | 24 |

TABLE 2-continued

In Vivo T.b.r. Activity of Antiprotozoan Dicationic Bichalcophenes.

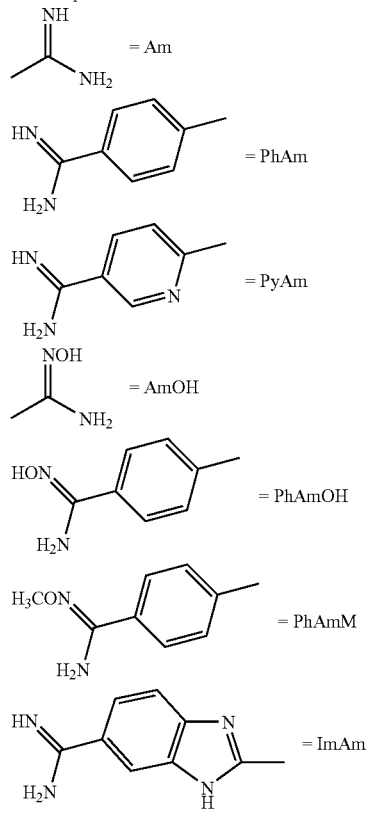

| Code | X | R | $R_1$ | Dosage route[a] | Dosage (mg/kg) | Cures[b] | Survival (days)[c] |
|---|---|---|---|---|---|---|---|
| 16 | O | PhAmOH | PhAmOH | po | 100 | 0/4 | 5.5 |

[a]ip = intraperitoneal; po = oral
[b]Number of mice that survive and are parasite free for 60 days.
[c]Average days of survival; untreated control animals die expire between day 7 and 8 post infection.

R and $R_1$:

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A compound of Formula (I):

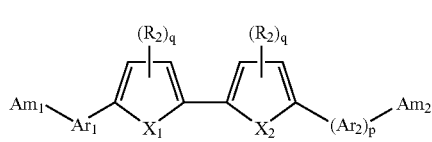

wherein:

$X_1$ and $X_2$ are independently selected from the group consisting of O, S, Se, Te, and $NR_1$, wherein $R_1$, is selected from the group consisting of H, alkyl, substituted alkyl, cycloalkyl, aryl, and substituted aryl;

p is an integer from 0 to 1;

each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;

$Ar_1$ and $Ar_2$ are independently selected from the group consisting of phenyl, pyridine, and benzimidazole;

$Am_1$ and $Am_2$ are each

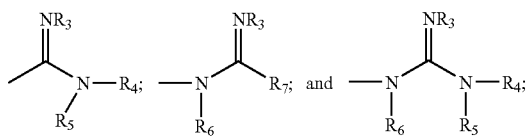

wherein:
  each $R_3$ is independently selected from the group consisting of H, hydroxyl, acyloxyl, and alkoxyl;
  each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_3$ and $R_4$ together represent a $C_2$ to $C_{10}$ alkyl, $C_2$ to $C_{10}$ hydroxyalkyl, or $C_2$ to $C_{10}$ alkylene; or
  $R_3$ and $R_4$ together are:

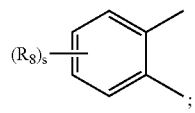

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

2. The compound of claim 1, wherein $Ar_1$ and $Ar_2$ are each independently selected from the group consisting of phenyl and pyridine and the compound of Formula (I) has the following structure:

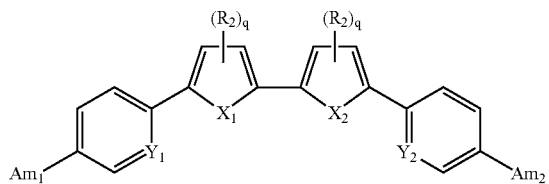

wherein:
  $X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
  $Y_1$ and $Y_2$ are each independently selected from the group consisting of CH and N;
  each q is independently an integer from 0 to 2;
  each $R_2$ is independently selected from the group consisting of alkyl, substituted alkyl, aryl, substituted aryl, halo, hydroxyl, alkoxyl, aryloxyl, and aralkyloxyl;

$Am_1$ and $Am_2$ are each

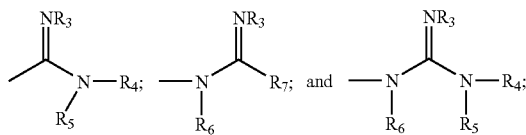

wherein:
  each $R_3$ is independently selected from the group consisting of H, hydroxyl, acyloxyl, and alkoxyl;
  each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_3$ and $R_4$ together represent a $C_2$ to $C_{10}$ alkyl, $C_2$ to $C_{10}$ hydroxyalkyl, or $C_2$ to $C_{10}$ alkylene; or
  $R_3$ and $R_4$ together are:

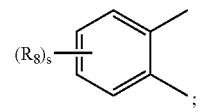

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;

or a pharmaceutically acceptable salt thereof.

3. The compound of claim 2, wherein the compound is selected from the group consisting of:
  5,5'-Bis-(4-N-hydroxybenzamidine)-2,2'-bifuran;
  5,5'-Bis-(4-amidinophenyl)-2,2'-bifuran;
  5,5'-Bis-[4-(N-methoxyamidino)phenyl]-2,2'-bifuran;
  5,5'-Bis-(4-amidino-2-pyridyl)-2,2'-bifuran;
  5,5'-Bis-[4-(N-methoxyamidino)-2-pyridyl]-2,2'-bifuran;
  5,5'-Bis-(4-amidinophenyl)-2,2'-bithiophene;
  5,5'-Bis-(4-amidino-2-pyridyl)-2,2'-bithiophene;
  5,5'-Bis-(4-amidinophenyl)-2,2'-biselenophene;
  5,5'-Bis-(4-amidino-2-pyridyl)-2,2'-biselenophene;
or a pharmaceutically acceptable salt thereof.

4. The compound of claim 2, wherein the pharmaceutically acceptable salt is selected from the group consisting of a hydrochloride salt, an acetate salt, and a maleate salt.

5. The compound of claim 1 wherein $Ar_1$ is selected from the group consisting of phenyl and pyridine, $Ar_2$ is benzimidazole, and the compound of Formula (I) has the following structure:

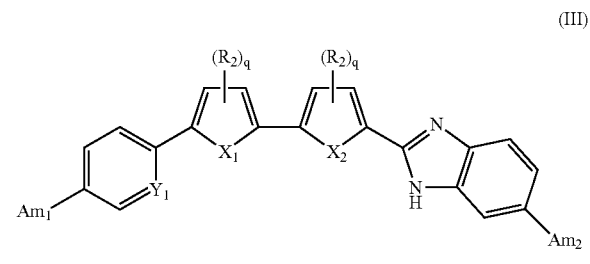

wherein:
X₁ and X₂ are independently selected from the group consisting of O, S, Se, Te, and NR₁, wherein R₁ is selected from the group consisting of H, alkyl, substituted alkyl, cycloalkyl, aryl, and substituted aryl;
Y₁ is selected from the group consisting of CH and N;
each q is independently an integer from 0 to 2;
each R₂ is independently selected from the group consisting of alkyl, substituted alkyl, aryl, substituted aryl, halo, hydroxyl, alkoxyl, aryloxyl, and aralkyloxyl;
Am₁ and Am₂ are each

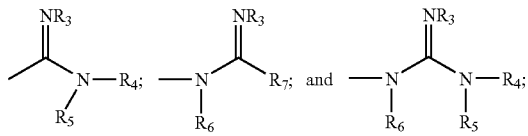

wherein:
each R₃ is independently selected from the group consisting of H, hydroxyl, acyloxyl, and alkoxyl;
each R₄, R₅, R₆, and R₇ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
R₃ and R₄ together represent a C₂ to C₁₀ alkyl, C₂ to C₁₀ hydroxyalkyl, or C₂ to C₁₀ alkylene; or
R₃ and R₄ together are:

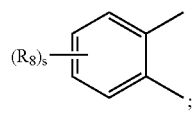

wherein s is a number from 1 to 4, and R₈ is H or —CONHR₉NR₁₀R₁₁, wherein R₉ is alkyl, and R₁₀ and R₁₁ are each independently selected from the group consisting of H and alkyl;
or a pharmaceutically acceptable salt thereof.

6. The compound of claim 5, wherein the compound is selected from the group consisting of

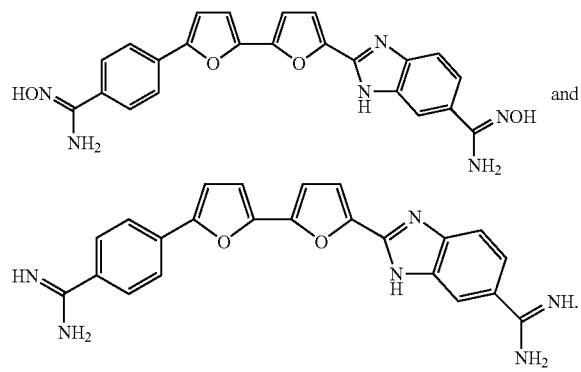

7. The compound of claim 5, wherein the pharmaceutically acceptable salt is an acetate salt.

8. The compound of claim 1, wherein p is 0 and the compound of Formula (I) has the following structure:

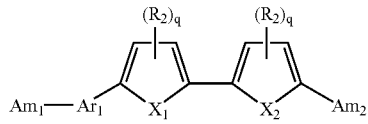

wherein:
X₁ and X₂ are independently selected from the group consisting of O, S, Se, Te, and NR₁, wherein R₁ is selected from the group consisting of H, alkyl, substituted alkyl, cycloalkyl, aryl, and substituted aryl;
Ar₁ is selected from the group consisting of phenyl, pyridine, and benzimidazole;
each q is independently an integer from 0 to 2;
each R₂ is independently selected from the group consisting of alkyl, substituted alkyl, aryl, substituted aryl, halo, hydroxyl, alkoxyl, aryloxyl, and aralkyloxyl;
Am₁ and Am₂ are each

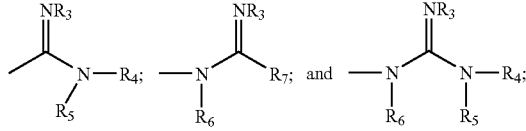

wherein:
each R₃ is independently selected from the group consisting of H, hydroxyl, acyloxyl, and alkoxyl;
each R₄, R₅, R₆, and R₇ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
R₃ and R₄ together represent a C₂ to C₁₀ alkyl, C₂ to C₁₀ hydroxyalkyl, or C₂ to C₁₀ alkylene; or
R₃ and R₄ together are:

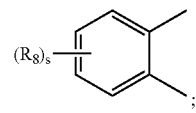

wherein s is a number from 1 to 4, and R₈ is H or —CONHR₉NR₁₀R₁₁, wherein R₉ is alkyl, and R₁₀ and R₁₁ are each independently selected from the group consisting of H and alkyl;
or a pharmaceutically acceptable salt thereof.

9. The compound of claim 8, wherein the compound is selected from the group consisting of:
N-Hydroxy-5'-[4-(N-hydroxyamidino)phenyl]-2,2'-bifuran-5-carboxamidine;
N-Acetoxy-5'-[4-(N-acetoxyamidino)phenyl]-2,2'-bifuran-5-carboxamidine;
5'-(4-Amidinophenyl)-2,2'-bifuran-5-carboxamidine;
N-Hydroxy-6-[5'-(N-hydroxyamidino)-2,2'-bifuran-5-yl]-nicotinamidine;
6-(5'-Amidino-2,2'-bifuran-5-yl)-nicotinamidine;
or a pharmaceutically acceptable salt thereof.

10. The compound of claim 8, wherein the pharmaceutically acceptable salt is a hydrochloride salt.

11. A pharmaceutical formulation comprising:
(a) a compound of claim 1; and
(b) a pharmaceutically acceptable carrier.

12. A method of treating a microbial infection in a subject in need of treatment thereof, the method comprising administering to the subject an effective amount of a compound of Formula (I):

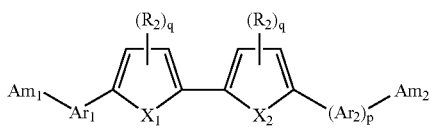
(I)

wherein:
$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
p is an integer from 0 to 1;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Ar_1$ and $Ar_2$ are independently selected from the group consisting of phenyl, pyridine, and benzimidazole;
$Am_1$ and $Am_2$ are each

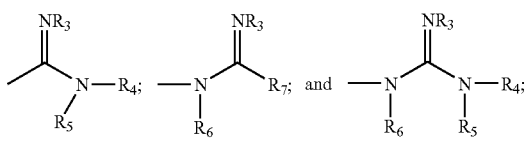

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

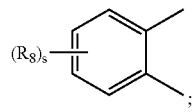

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;
or a pharmaceutically acceptable salt thereof.

13. The method of claim 12, wherein $Ar_1$ and $Ar_2$ are each independently selected from the group consisting of phenyl and pyridine and the compound of Formula (I) has the following structure:

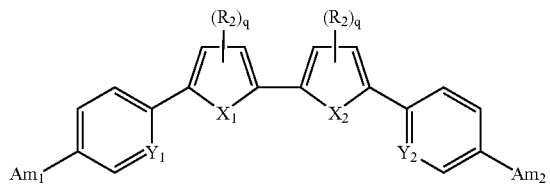
(II)

wherein:
$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
$Y_1$ and $Y_2$ are each independently selected from the group consisting of CH and N;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Am_1$ and $Am_2$ are each

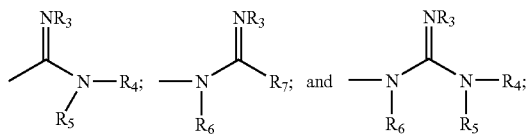

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

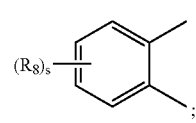

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;
or a pharmaceutically acceptable salt thereof.

14. The method of claim 13, wherein the compound is selected from the group consisting of:
5,5'-Bis-(4-N-hydroxybenzamidine)-2,2'-bifuran;
5,5'-Bis-(4-amidinophenyl)-2,2'-bifuran;
5,5'-Bis-[4-(N-methoxyamidino)phenyl]-2,2'-bifuran;
5,5'-Bis-(4-amidino-2-pyridyl)-2,2'-furan;
5,5'-Bis-[4-(N-methoxyamidino)-2-pyridyl]-2,2'-bifuran;
5,5'-Bis-(4-amidinophenyl)-2,2'-bithiophene;
5,5'-Bis-(4-amidino-2-pyridyl)-2,2'-bithiophene;
5,5'-Bis-(4-amidinophenyl)-2,2'-biselenophene;

5,5'-Bis-(4-amidino-2-pyridyl)-2,2'-biselenophene;
or a pharmaceutically acceptable salt thereof.

15. The method of claim 12, wherein Ar$_1$ is selected from the group consisting of phenyl and pyridine and Ar$_2$ is benzimidazole and the compound of Formula (I) has the following structure:

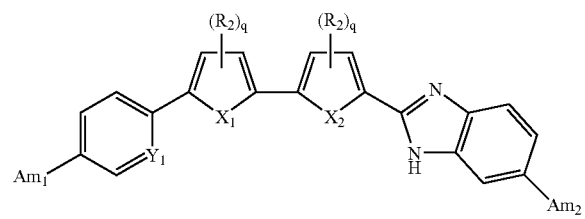

wherein:
- X$_1$ and X$_2$ are independently selected from the group consisting of O, S, Se, Te, and NR$_1$, wherein R$_1$ is selected from the group consisting of H, alkyl, substituted alkyl, cycloalkyl, aryl, and substituted aryl;
- Y$_1$ is selected from the group consisting of CH and N;
- each q is independently an integer from 0 to 2;
- each R$_2$ is independently selected from the group consisting of alkyl, substituted alkyl, aryl, substituted aryl, halo, hydroxyl, alkoxyl, aryloxyl, and aralkyloxyl;
- Am$_1$ and Am$_2$ are each

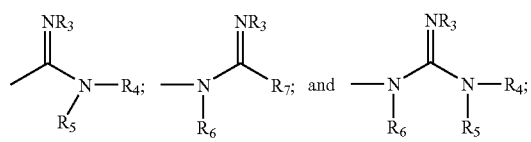

wherein:
- each R$_3$ is independently selected from the group consisting of H, hydroxyl, acyloxyl, and alkoxyl;
- each R$_4$, R$_5$, R$_6$, and R$_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
- R$_3$ and R$_4$ together represent a C$_2$ to C$_{10}$ alkyl, C$_2$ to C$_{10}$ hydroxyalkyl, or C$_2$ to C$_{10}$ alkylene; or
- R$_3$ and R$_4$ together are:

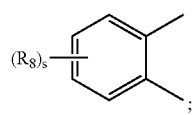

wherein s is a number from 1 to 4, and R$_8$ is H or —CONHR$_9$NR$_{10}$R$_{11}$, wherein R$_9$ is alkyl, and R$_{10}$ and R$_{11}$ are each independently selected from the group consisting of H and alkyl;

or a pharmaceutically acceptable salt thereof.

16. The method of claim 15, wherein the compound is selected from the group consisting of:

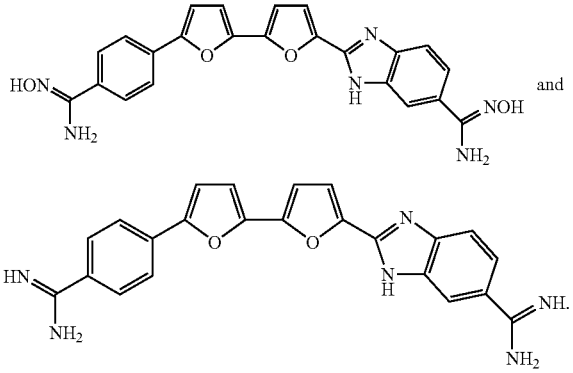

17. The method of claim 12, wherein p is 0 and the compound of Formula (I) has the following structure:

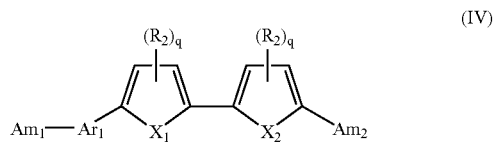

wherein:
- X$_1$ and X$_2$ are independently selected from the group consisting of O, S, Se, Te, and NR$_1$, wherein R$_1$ is selected from the group consisting of H, alkyl, substituted alkyl, cycloalkyl, aryl, and substituted aryl;
- Ar$_1$ is selected from the group consisting of phenyl, pyridine, and benzimidazole;
- each q is independently an integer from 0 to 2;
- each R$_2$ is independently selected from the group consisting of alkyl, substituted alkyl, aryl, substituted aryl, halo, hydroxyl, alkoxyl, aryloxyl, and aralkyloxyl;
- Am$_1$ and Am$_2$ are each

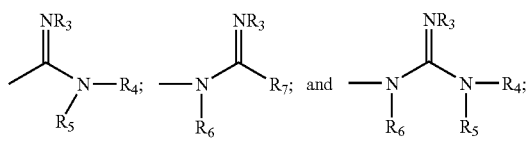

wherein:
- each R$_3$ is independently selected from the group consisting of H, hydroxyl, acyloxyl, and alkoxyl;
- each R$_4$, R$_5$, R$_6$, and R$_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
- R$_3$ and R$_4$ together represent a C$_2$ to C$_{10}$ alkyl, C$_2$ to C$_{10}$ hydroxyalkyl, or C$_2$ to C$_{10}$ alkylene; or $R_3$ and $R_4$ together are:

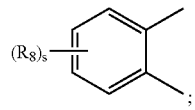

wherein s is a number from 1 to 4, and $R_8$ is H or —CONHR$_9$NR$_{10}$R$_{11}$, wherein $R_9$ is alkyl, and $R_{10}$ and $R_{11}$ are each independently selected from the group consisting of H and alkyl;
or a pharmaceutically acceptable salt thereof.

18. The method of claim 17, wherein the compound is selected from the group consisting of:
N-Hydroxy-5'-[4-(N-hydroxyamidino)phenyl]-2,2'-bifuran-5-carboxamidine;
N-Acetoxy-5'-[4-(N-acetoxyamidino)phenyl]-2,2'-bifuran-5-carboxamidine;
5'-(4-Amidinophenyl)-2,2'-bifuran-5-carboxamidine;
N-Hydroxy-6-[5'-(N-hydroxyamidino)-2,2'-bifuran-5-yl]-nicotinamidine;
6-(5'-Amidino-2,2'-bifuran-5-yl)-nicotinamidine;
or a pharmaceutically acceptable salt thereof.

19. The method of claim 12, wherein the microbial infection is selected from the group consisting of a *Trypanosoma* species infection, a *Plasmodium* species infection, and a *Leishmania* species infection.

20. The method of claim 19, wherein the *Trypanosoma* species is selected from the group consisting of *Trypanosoma brucei rhodesiense*, *Trypanosoma brucei gambiense*, *Trypanosoma brucei brucei*, and *Trypanosoma cruzi*.

21. The method of claim 19, wherein the *Plasmodium* species is *Plasmodium falciparum*.

22. The method of claim 19, wherein the *Leishmania* species is selected from the group consisting of *Leishmania donovani* and *Leishmania mexicana amazonensis*.

23. The method of claim 12, wherein the compound of Formula (I) is administered in the form of a pharmaceutically acceptable salt.

24. The method of claim 23, wherein the pharmaceutically acceptable salt is selected from the group consisting of a hydrochloride salt, an acetate salt and a maleate salt.

25. The method of claim 12, wherein the compound of Formula (I) is administered prophylactically to prevent or reduce the incidence of one of:
(a) a microbial infection in a subject at risk of infection;
(b) a recurrence of the microbial infection; and
(c) combinations thereof.

26. A method for preparing a compound of Formula (I)

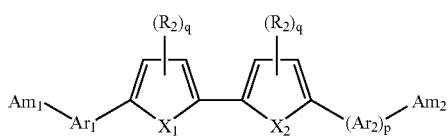

(I)

wherein:
$X_1$ and $X_2$ are independently selected from the group consisting of O, S, Se, Te, and NR$_1$, wherein $R_1$ is selected from the group consisting of H, alkyl, substituted alkyl, cycloalkyl, aryl, and substituted aryl;
p is an integer from 0 to 1;
each q is independently an integer from 0 to 2;

each $R_2$ is independently selected from the group consisting of alkyl, substituted alkyl, aryl, substituted aryl, halo, hydroxyl, alkoxyl, aryloxyl, and aralkyloxyl;
Ar$_1$ and Ar$_2$ are independently selected from the group consisting of phenyl, pyridine, and benzimidazole;
Am$_1$ and Am$_2$ are each

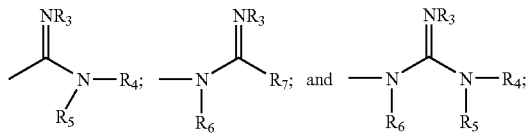

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

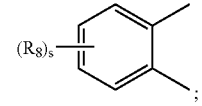

wherein s is a number from 1 to 4, and $R_8$ is H or —CONHR$_9$NR$_{10}$R$_{11}$, wherein $R_9$ is alkyl, and $R_{10}$ and $R_{11}$ are each independently selected from the group consisting of H and alkyl;
or a pharmaceutically acceptable salt thereof;
the method comprising:
(a) contacting a first cyano-substituted heterocyclic compound with N-bromosuccinimide to form a first bromo-heterocyclic compound;
(b) coupling the first bromo-heterocyclic compound with a second heterocyclic compound to form a third heterocyclic compound;
(c) reacting the third heterocyclic compound with one of:
(i) a strong acid and an anhydrous alcohol, followed by ammonia and an anhydrous alcohol to form a compound of Formula (I), wherein the compound of Formula (I) is a bis-amidine;
(ii) hydroxylamine hydrochloride and a base to form a compound of Formula (I), wherein the compound of Formula (I) is a bis-amidoxime; and
(iii) a lithium bis(trialkylsilyl)amide for a period of time, followed by a strong acid for a period of time to form a compound of Formula (I), wherein the compound of Formula (I) is a bis-amidine.

27. The method of claim 26, comprising:
(a) reacting the third heterocyclic compound with N-bromosuccinimide to form a second bromo-heterocyclic compound;
(b) contacting the second bromo-heterocyclic compound with one of:
(i) cuprous cyanide to form a dinitrile; and
(ii) a cyano-substituted arylboronic acid and a palladium catalyst to form a dinitrile;

(c) reacting the dinitrile with one of:
  (i) a strong acid and an anhydrous alcohol to form an intermediate di-imidate, followed by ammonia and an anhydrous alcohol to form a compound of Formula (I), wherein the compound of Formula (I) is a bis-amidine;
  (ii) hydroxylamine hydrochloride and a base to form a compound of Formula (I), wherein the compound of Formula (I) is a bis-amidoxime; and
  (iii) a lithium bis(trialkylsilyl)amide for a period of time, followed by a strong acid and an alcohol for a period of time to form a compound of Formula (I), wherein the compound of Formula (I) is a bis-amidine.

28. The method of claim 26, comprising:
(a) reacting the third heterocyclic compound with phosphorus oxychloride to form a heterocyclic aldehyde;
(b) contacting the heterocyclic aldehyde with 3,4-diaminobenzonitrile and 1,4-benzoquinone to form a benzimidazole;
(c) reacting the benzimidazole with one of the following:
  (i) a strong acid and an alcohol to form an intermediate di-imidate, followed by ammonia and an alcohol to form a compound of Formula (I), wherein the compound of Formula (I) is a bis-amidine;
  (ii) hydroxylamine hydrochloride and a base to form a compound of Formula (I), wherein the compound of Formula (I) is a bis-amidoxime; and
  (iii) a lithium bis(trialkylsilyl)amide for a period of time, followed by hydrochloric acid for a period of time to form a compound of Formula (I), wherein the compound of Formula (I) is a bis-amidine.

29. The method of claim 26, comprising:
(a) contacting the first bromo-heterocyclic compound with hydroxylamine hydrochloride and a base to form an amidoxime;
(b) alkylating the amidoxime with a dialkyl sulfate to form a N-alkoxyamidine; and
(c) coupling two N-alkoxyamidines to form a compound of Formula (I), wherein the compound of Formula (I) is a bis-N-alkoxyamidine.

30. The method of claim 26, comprising:
(a) contacting the first bromo-heterocyclic compound with cuprous cyanide to form a dinitrile; and
(b) contacting the dinitrile with hydroxylamine hydrochloride and a base to form a compound of Formula (I), wherein the compound of Formula (I) is a bis-amidoxime.

31. The method of claim 26, wherein the first cyano-substituted heterocyclic compound is selected from the group consisting of:
2-(4-cyanophenyl)furan,
6-(furan-2-yl)nicotinonitrile,
2-(4-cyanophenyl)thiophene,
6-(thiophen-2-yl)nicotinonitrile,
2-(4-cyanophenyl)selenophene,
6-(selenophen-2-yl)nicotinonitrile, and
2-(4-cyanophenyl)-5-(thiophen-2-yl)thiophene.

32. A method for preparing a compound of Formula (I)

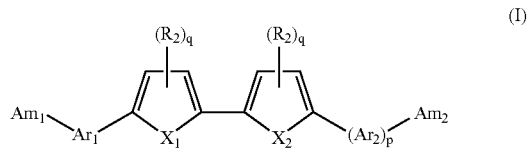

wherein:
$X_1$ and $X_2$ are independently selected from the group consisting of O, S, Se, Te, and $NR_1$, wherein $R_1$ is selected from the group consisting of H, alkyl, substituted alkyl, cycloalkyl, aryl, and substituted aryl;
p is an integer from 0 to 1;
each q is independently an integer from 0 to 2;
each $R_2$ is independently selected from the group consisting of alkyl, substituted alkyl, aryl, substituted aryl, halo, hydroxyl, alkoxyl, aryloxyl, and aralkyloxyl;
$Ar_1$ and $Ar_2$ are independently selected from the group consisting of phenyl, pyridine, and benzimidazole;
$Am_1$ and $Am_2$ are each

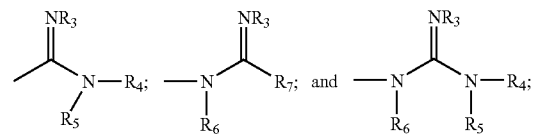

wherein:
each $R_3$ is independently selected from the group consisting of H, hydroxyl, acyloxyl, and alkoxyl;
each $R_4$, $R_5$, $R_6$, and $R_7$ is independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_3$ and $R_4$ together represent a $C_2$ to $C_{10}$ alkyl, $C_2$ to $C_{10}$ hydroxyalkyl, or $C_2$ to $C_{10}$ alkylene; or
$R_3$ and $R_4$ together are:

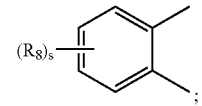

wherein s is a number from 1 to 4, and $R_8$ is H or —$CONHR_9NR_{10}R_{11}$, wherein $R_9$ is alkyl, and $R_{10}$ and $R_{11}$ are each independently selected from the group consisting of H and alkyl;
or a pharmaceutically acceptable salt thereof;
the method comprising:
(a) contacting a halo-substituted five-membered aromatic heterocyclic aldehyde with hydroxylamine hydrochloride and acetic anhydride to form a 2-cyano-5-halo-heteroaryl compound;
(b) coupling the 2-cyano-5-halo-heteroaryl compound with a trialkyltin-substituted five-membered aromatic heterocyclic acetal to form a cyano-substituted diaryl aldehyde, (b) contacting the cyano-substituted diaryl aldehyde with 3,4-diaminobenzonitrile and 1,4-benzoquinone to form a benzimidazole;

(c) contacting the benzimidazole with one of:
  (i) a strong acid and an alcohol to form an intermediate di-imidate, followed by ammonia and an alcohol to form a compound of Formula (I), wherein the compound of Formula (I) is a bis-amidine;
  (ii) hydroxylamine hydrochloride and a base to form a compound of Formula (I), wherein the compound of Formula (I) is a bis-amidoxime; and
  (iii) a lithium bis(trialkylsilyl)amide for a period of time, followed by a strong acid for a period of time to form a compound of Formula (I), wherein the compound of Formula (I) is a bis-amidine.

33. The method of claim 26, claim 27, claim 28, claim 30, or claim 32 further comprising:
  (a) contacting the bis-amidoxime with acetic acid and acetic anhydride to form a compound of Formula (I), wherein the compound of Formula (I) is a bis-acetoxyamidine; and
  (b) contacting the bis-acetoxyamidine with a palladium-on-carbon catalyst, hydrogen gas, acetic acid, and an alcohol to form a compound of Formula (I), wherein the compound of Formula (I) is a diamidine.

* * * * *